(12) United States Patent
Moffett et al.

(10) Patent No.: US 8,629,247 B2
(45) Date of Patent: Jan. 14, 2014

(54) ANTIBODIES AGAINST PROSTATE SPECIFIC MEMBRANE ANTIGEN

(75) Inventors: Serge Moffett, St-Laurent (CA); Dominic Melançon, Blainville (CA); Uri H. Saragovi, Montréal (CA); Phil Gold, Westmount (CA); Claudio A. Cuello, Westmount (CA)

(73) Assignee: Proscan RX Pharma Inc., Montreal, Quebec (CA)

( * ) Notice: Subject to any disclaimer, the term of this patent is extended or adjusted under 35 U.S.C. 154(b) by 220 days.

(21) Appl. No.: 13/264,652

(22) PCT Filed: Apr. 14, 2010

(86) PCT No.: PCT/CA2010/000567
§ 371 (c)(1),
(2), (4) Date: Dec. 2, 2011

(87) PCT Pub. No.: WO2010/118522
PCT Pub. Date: Oct. 21, 2010

(65) Prior Publication Data
US 2012/0093719 A1    Apr. 19, 2012

Related U.S. Application Data

(60) Provisional application No. 61/202,867, filed on Apr. 14, 2009, provisional application No. 61/249,094, filed on Oct. 6, 2009.

(51) Int. Cl.
*C07K 16/00* (2006.01)

(52) U.S. Cl.
USPC .................. 530/387.3; 530/387.7; 530/391.3

(58) Field of Classification Search
None
See application file for complete search history.

(56) References Cited

FOREIGN PATENT DOCUMENTS

| EP | 1790663 A1 | 5/2007 |
|---|---|---|
| WO | WO 93/02191 | 2/1993 |
| WO | WO 2004/035537 A2 | 4/2004 |
| WO | WO 2008/150841 A1 | 12/2008 |

OTHER PUBLICATIONS

International Search Report for PCT/CA10/000567, mailed Aug. 2, 2010 (6 pages).

Moffett, et al. "Preparation and Characterization of New Anti-PSMA Monoclonal Antibodies with Potential Clinical Use," HYBRIDOMA, Dec. 2007, vol. 26, No. 6; pp. 363-372. Montreal, Quebec, Canada (10 pages).

*Primary Examiner* — Sheela J Huff
(74) *Attorney, Agent, or Firm* — Fangli Chen; Robert N. Sahr; Choate, Hall & Stewart LLP

(57) ABSTRACT

Antibodies (Ab) and antigen binding fragments capable of binding to prostate specific membrane antigen and which may be used for diagnostic and therapeutic purposes are provided herein. Formulation anti-PSMA antibodies which are stable under extreme storage condition are also provided.

15 Claims, 10 Drawing Sheets

FIGURE 1

HEAVY CHAIN VARIABLE REGION of mAb1

Nucleotide sequence (SEQ ID NO:1):
gaggttcagctgcagcagtctggggcagagcttgtgaagccaggggcctcagtcaagttgtcctg
cacagcttctggcttcaacattaaagacacctatatgcactgggtgaaacagaggcctgaacagg
gcctggagtggattggagggattgatcctgcggatggtgagactaaatatgacccgaagttccag
gacaaggccactataacaacagacacatcctccaatacagtctacctgcagatcagcagcctgac
atctgaggacactgccgtctattactgtgttaggagttttgactactggggccaaggcaccactc
tcacagtctcctcagccaaaacgacacccca

Amino acid sequence (SEQ ID NO:2)
EVQLQQSGAELVKPGASVKLSCTASGFNIKDTYMHWVKQRPEQGLEWIGGIDPADGETKYDPKFQ
DKATITTDTSSNTVYLQISSLTSEDTAVYYCVRSFDYWGQGTTLTVSSAKTTPP

LIGHT CHAIN VARIABLE REGION of mAb1

Nucleotide sequence (SEQ ID NO:3)
gatgttgtgatgacccaaactccactctccctgcctgtcagtcttggagatcaagcctccatctc
ttgcagatctagtcagagccttgtacacagtaatggaaacacctatttacattggtacctgcaaa
aaccaggccagtctccaaagtcctgatctacaaagcttccaatcgatttctggggtcccagac
aggttcagtggccgtggatcagggacagatttcacactcaagatcagcagagtggaggctgagga
tctgggagtttatttctgcttcaaagtacacatgttccgtacacgttcggaggggggaccaagc
tggaaataaaacgggctgatgctgcacca

Amino acid sequence (SEQ ID NO:4)
DVVMTQTPLSLPVSLGDQASISCRSSQSLVHSNGNTYLHWYLQKPGQSPKFLIYKASNRFSGVPD
RFSGRGSGTDFTLKISRVEAEDLGVYFCFQSTHVPYTFGGGTKLEIKRADAAP

CDRH1 (SEQ ID NO:5)
GFNIKDTYMH

CDRH2 (SEQ ID NO:6)
GIDPADGETK

CDRH3 (SEQ ID NO:7)
VRSFDY

CDRL1 (SEQ ID NO:8)
RSSQSLVHSNGNTYLH

CDRL2 (SEQ ID NO:9)
KASNRFS

CDRL3 (SEQ ID NO:10)
FQSTHVPYT

FIGURE 2

HEAVY CHAIN VARIABLE REGION of mAb2 Nucleotide sequence (SEQ ID NO.:19)
ATGAAATGCAGCTGGGTTATCTTCTTCCTGATGGCAGTGGTTACAGGGGTCGATGCAGAGGTTCACCTGCA
GCAGTCTGGGGCAGAGCTTGTGAAGCCAGGGGCCTCAGTCAAGTTGTCCTGCACAGCCTCTGGCTTCAGTA
TTAGAGACACCTATATGCACTGGGTGAGGCAGAGGCCTGAACAGGGCCTGGAATGGATTACAGGGATTGAT
CCTGAAAATGGTAATTCTAAATATGCCCCGAGGTTCCAGGACAAGGCCACTATAATAGCAGACACGTCCTC
CAACACAGTTCACCTGCAGCTCGACACCCTGACATCTGAGGACACTGCCGTCTATTATTGTACTAGGGAGC
TTGCTTACTGGGCCCAAGGGACTCGGGTCACTGTCTCTGCA

Amino acid sequence (SEQ ID NO.:11)
MKCSWVIFFLMAVVTGVDAEVHLQQSGAELVKPGASVKLSCTASGFSIRDTYMHWVRQRPEQGLE
WITGIDPENGNSKYAPRFQDKATIIADTSSNTVHLQLDTLTSEDTAVYYCTRELAYWAQGTRVTV
SA

LIGHT CHAIN VARIABLE REGION of mAb2
Nucleotide sequence (SEQ ID NO.:20)
ATGATGAGTCCTGCCCAGTTCCTGTTTCTGTTAGTGCTCTGGATTCGGGAGAACAACGGTGATGTTGTGAT
GACCCAGATTCCACTCACTTTGTCGCTTACCATTGGACAACCAGCCTCCATCTCTTGCAAGTCAAGTCAGA
GTCTCTTACATCGTGATGGAAAGACATATTTGAATTGGTTGTTACAGAGGCCACGCCAGTCTCCAAAGCCCC
CTAATGTATCTGGTGTCTAAACTGGACTCTGGAGTCCCTGATAGGTTCACTGGCAGTGGATCAGGGACAGA
GTTCACACTGAAAATCAGCAGAGTGGAGGCTGAAGATTTGGGAGTTTATTATTGCTGGCAAGGTACACATT
TTCCTCGGACGTTCGGTGGAGGCACCAAGCTGGAAATCAAA amino acid sequence(SEQ ID NO.:12)
MMSPAQFLFLLVLWIRENNGDVVMTQIPLTLSLTIGQPASISCKSSQSLLHRDGKTYLNWLLQRP
GQSPKRLMYLVSKLDSGVPDRFTGSGSGTEFTLKISRVEAEDLGVYYCWQGTHFPRTFGGGTKLE
IK

CDRH1 (SEQ ID NO.:13)
GFSIRDTYMH

CDRH2 (SEQ ID NO.:14)
GIDPENGNSK

CDRH3 (SEQ ID NO.:15)
ELAY

CDRL1 (SEQ ID NO.:16)
KSSQSLLHRDGKTYLN

CDRL2 (SEQ ID NO.:17)
LVSKLDS

CDRL3 (SEQ ID NO.:18)
WQGTHFPRT

FIGURE 3

| Light chain variable region | SEQ ID NO.: | Heavy chain variable region | SEQ ID NO.: | |
|---|---|---|---|---|
| DVVLTQTPLNLSVTIGQPASISCKSSQSLLHSDGKTYLNWLLQRPG QSPKRLMYLVSRLDSGVPDRFTGSGSGTDFTLKISRVEAEDLGVYY CWQGTHFPRTFGGGTKLEIK | 21 | EVQLQQSGAELVKPGASVKLSCTASGFYIKDTYI HWVKQRPEEVLEWIGGIDPADGDTRYDPKFQGKA TITADTSSNSAYLHLTSLLTSEDTAVYFCARELAY WGQGTLVTVSA | 22 | MAb3 |
| EAVMTQTPLTLSVIIGQPASFSCKSSHSLLHRDGRTYLNWLLQRPG QSPQRLIYLVSKLDSGVPDRFTGSGSGTDFTLKISRVEAEDLGVYY CWQGTHFPRTFGGGTKLEIK | 23 | EVQLQQSGAEFVRPGAAVKLSCTVSGLNIKDSYL HWVKQRPEQGLEWIGGIDPANGDVEYDPKFQGKA AITADTSSNTAYLRLSSLTSEDTAVYYCAFFPYW GQGTLVTVSA | 24 | MAb6 |
| DAVLTQTPLTLSVTIGHPASISCKSSQSLLHRDGKTYLNWVFQRPG QSPQRLIYLVSLVDSGVPDRFTGSGSGTDFTLKINRVEAEDLGVYY CWQGTHFPRTFGGGTKLEIK | 25 | GVQLQQSGAELVKPGASVKLSCTGSGFNIKDTYM HWVKQRPEQGLEWIGGIDPENGNTKFDPRFQDKA TITADTSSNTVLLQLSSLTSEDTAVYYCANLGRP FAHWGQGT LVTVSA | 26 | MAb4 |
| DIVMSQSPSSLAVSAGEKVTMSCKSSQSLLNSRTRKNYLAWYQQKL GQSPKLLIYWASTRESGVPDRFTGSGSGTDFTLTISSVQAEDLAVY YCKQSYNFITFGAGTKLELK | 27 | EVQLQQSGPDLVKPGASVKVSCKASGYTFTVYVI HWVIQKPGQGLEWIGYINPYNDGAEYNENFKGKA TLTSDKSSSTAYMELSSLTSEDSAVYYCTRGENY YTSRYGFFDVWGAGTTVTVSS | 28 | MAb5 |

FIGURE 10

Light chain:

DVVMTQTPLSLPVSLGDQASISCRSSQSLVHSNGNTYLHWYLQKPGQSPKFLIYKASNRFSGVPDRFSGR
GSGTDFTLKISRVEAEDLGVYFCFQSTHVPYTFGGGTKLEIKRTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPVTKS
FNRGEC

Heavy chain

EVQLQQSGAELVKPGASVKLSCTASGFNIKDTYMHWVKQRPEQGLEWIGGIDPADGETKYDPKFQDKATI
TTDTSSNTVYLQISSLTSEDTAVYYCVRSFDYWGQGTTLTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGN
VFSCSVMHEALHNHYTQKSLSLSPGK

FIGURE 11A

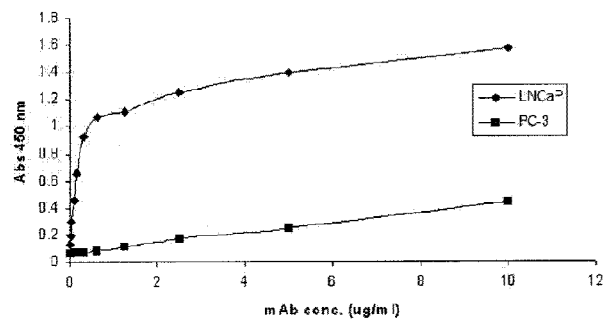

FIGURE 11B

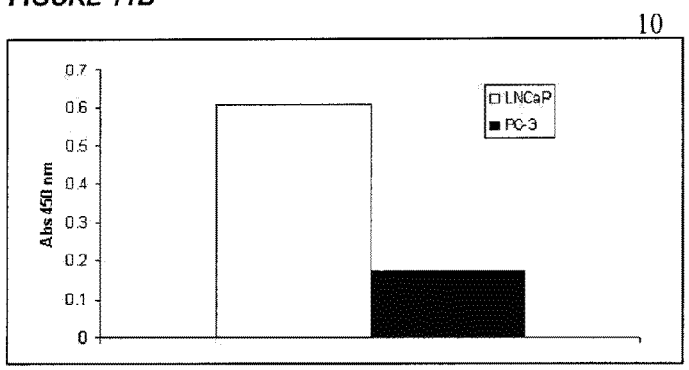

SEQUENCE LISTING

```
<160> NUMBER OF SEQ ID NOS: 31

<210> SEQ ID NO 1
<211> LENGTH: 357
<212> TYPE: DNA
<213> ORGANISM: Mus musculus

<400> SEQUENCE: 1
gaggttcagc tgcagcagtc tggggcagag cttgtgaagc caggggcctc agtcaagttg      60
tcctgcacag cttctggctt caacattaaa gacacctata tgcactgggt gaaacagagg     120
cctgaacagg gcctggagtg gattggaggg attgatcctg cggatggtga gactaaatat     180
gacccgaagt tccaggacaa ggccactata acaacagaca catcctccaa tacagtctac     240
ctgcagatca gcagcctgac atctgaggac actgccgtct attactgtgt taggagtttt     300
gactactggg gccaaggcac cactctcaca gtctcctcag ccaaaacgac acccca        357

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Ala Glu Leu Val Lys Pro Gly Ala
1               5                   10                  15
```

```
Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
            35                  40                  45

Gly Gly Ile Asp Pro Ala Asp Gly Glu Thr Lys Tyr Asp Pro Lys Phe
 50                  55                  60

Gln Asp Lys Ala Thr Ile Thr Thr Asp Thr Ser Asn Thr Val Tyr
 65                  70                  75                  80

Leu Gln Ile Ser Ser Leu Thr Ser Glu Asp Thr Ala Val Tyr Tyr Cys
 85                  90                  95

Val Arg Ser Phe Asp Tyr Trp Gly Gln Gly Thr Thr Leu Thr Val Ser
                100                 105                 110

Ser Ala Lys Thr Thr Pro Pro
            115
```

<210> SEQ ID NO 3
<211> LENGTH: 354
<212> TYPE: DNA
<213> ORGANISM: Mus musculus

<400> SEQUENCE: 3

```
gatgttgtga tgacccaaac tccactctcc ctgcctgtca gtcttggaga tcaagcctcc      60
atctcttgca gatctagtca gagccttgta cacagtaatg aaacacccta tttacattgg     120
tacctgcaaa aaccaggcca gtctccaaag ttcctgatct acaaagcttc caatcgattt     180
tctggggtcc cagacaggtt cagtggccgt ggatcaggga cagatttcac actcaagatc     240
agcagagtgg aggctgagga tctgggagtt tatttctgct ttcaaagtac acatgttccg     300
tacacgttcg gaggggggac caagctggaa ataaaacggg ctgatgctgc acca           354
```

<210> SEQ ID NO 4
<211> LENGTH: 118
<212> TYPE: PRT
<213> ORGANISM: Mus musculus

<400> SEQUENCE: 4

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Phe Leu Ile Tyr Lys Ala Ser Asn Arg Phe Ser Gly Val Pro
 50                  55                  60

Asp Arg Phe Ser Gly Arg Gly Ser Gly Thr Asp Phe Thr Leu Lys Ile
 65                  70                  75                  80

Ser Arg Val Glu Ala Glu Asp Leu Gly Val Tyr Phe Cys Phe Gln Ser
            85                  90                  95

Thr His Val Pro Tyr Thr Phe Gly Gly Gly Thr Lys Leu Glu Ile Lys
                100                 105                 110

Arg Ala Asp Ala Ala Pro
            115
```

<210> SEQ ID NO 5
<211> LENGTH: 10
<212> TYPE: PRT
<213> ORGANISM: Mus musculus

<400> SEQUENCE: 5

Gly Phe Asn Ile Lys Asp Thr Tyr Met His
1               5                   10

<210> SEQ ID NO 6
<211> LENGTH: 10
<212> TYPE: PRT
<213> ORGANISM: Mus musculus

<400> SEQUENCE: 6

Gly Ile Asp Pro Ala Asp Gly Glu Thr Lys
1               5                   10

<210> SEQ ID NO 7
<211> LENGTH: 6
<212> TYPE: PRT
<213> ORGANISM: Mus musculus

<400> SEQUENCE: 7

Val Arg Ser Phe Asp Tyr
1               5

<210> SEQ ID NO 8
<211> LENGTH: 16
<212> TYPE: PRT
<213> ORGANISM: Mus musculus

<400> SEQUENCE: 8

Arg Ser Ser Gln Ser Leu Val His Ser Asn Gly Asn Thr Tyr Leu His
1               5                   10                  15

<210> SEQ ID NO 9
<211> LENGTH: 7
<212> TYPE: PRT
<213> ORGANISM: Mus musculus

<400> SEQUENCE: 9

Lys Ala Ser Asn Arg Phe Ser
1               5

<210> SEQ ID NO 10
<211> LENGTH: 9
<212> TYPE: PRT
<213> ORGANISM: Mus musculus

<400> SEQUENCE: 10

Phe Gln Ser Thr His Val Pro Tyr Thr
1               5

<210> SEQ ID NO 11
<211> LENGTH: 132
<212> TYPE: PRT
<213> ORGANISM: Mus musculus

<400> SEQUENCE: 11

Met Lys Cys Ser Trp Val Ile Phe Phe Leu Met Ala Val Val Thr Gly
1               5                   10                  15

Val Asp Ala Glu Val His Leu Gln Gln Ser Gly Ala Glu Leu Val Lys
                20                  25                  30

Pro Gly Ala Ser Val Lys Leu Ser Cys Thr Ala Ser Gly Phe Ser Ile
            35                  40                  45

Arg Asp Thr Tyr Met His Trp Val Arg Gln Arg Pro Glu Gln Gly Leu
        50                  55                  60

Glu Trp Ile Thr Gly Ile Asp Pro Glu Asn Gly Asn Ser Lys Tyr Ala

```
            65                  70                  75                  80
Pro Arg Phe Gln Asp Lys Ala Thr Ile Ile Ala Asp Thr Ser Ser Asn
                85                  90                  95

Thr Val His Leu Gln Leu Asp Thr Leu Thr Ser Glu Asp Thr Ala Val
            100                 105                 110

Tyr Tyr Cys Thr Arg Glu Leu Ala Tyr Trp Ala Gln Gly Thr Arg Val
        115                 120                 125

Thr Val Ser Ala
    130

<210> SEQ ID NO 12
<211> LENGTH: 132
<212> TYPE: PRT
<213> ORGANISM: Mus musculus

<400> SEQUENCE: 12

Met Met Ser Pro Ala Gln Phe Leu Phe Leu Leu Val Leu Trp Ile Arg
1               5                   10                  15

Glu Asn Asn Gly Asp Val Val Met Thr Gln Ile Pro Leu Thr Leu Ser
            20                  25                  30

Leu Thr Ile Gly Gln Pro Ala Ser Ile Ser Cys Lys Ser Ser Gln Ser
        35                  40                  45

Leu Leu His Arg Asp Gly Lys Thr Tyr Leu Asn Trp Leu Leu Gln Arg
    50                  55                  60

Pro Gly Gln Ser Pro Lys Arg Leu Met Tyr Leu Val Ser Lys Leu Asp
65                  70                  75                  80

Ser Gly Val Pro Asp Arg Phe Thr Gly Ser Gly Ser Gly Thr Glu Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys
    130

<210> SEQ ID NO 13
<211> LENGTH: 10
<212> TYPE: PRT
<213> ORGANISM: Mus musculus

<400> SEQUENCE: 13

Gly Phe Ser Ile Arg Asp Thr Tyr Met His
1               5                   10

<210> SEQ ID NO 14
<211> LENGTH: 10
<212> TYPE: PRT
<213> ORGANISM: Mus musculus

<400> SEQUENCE: 14

Gly Ile Asp Pro Glu Asn Gly Asn Ser Lys
1               5                   10

<210> SEQ ID NO 15
<211> LENGTH: 4
<212> TYPE: PRT
<213> ORGANISM: Mus musculus

<400> SEQUENCE: 15

Glu Leu Ala Tyr
```

<210> SEQ ID NO 16
<211> LENGTH: 16
<212> TYPE: PRT
<213> ORGANISM: Mus musculus

<400> SEQUENCE: 16

Lys Ser Ser Gln Ser Leu Leu His Arg Asp Gly Lys Thr Tyr Leu Asn
1               5                   10                  15

<210> SEQ ID NO 17
<211> LENGTH: 7
<212> TYPE: PRT
<213> ORGANISM: Mus musculus

<400> SEQUENCE: 17

Leu Val Ser Lys Leu Asp Ser
1               5

<210> SEQ ID NO 18
<211> LENGTH: 9
<212> TYPE: PRT
<213> ORGANISM: Mus musculus

<400> SEQUENCE: 18

Trp Gln Gly Thr His Phe Pro Arg Thr
1               5

<210> SEQ ID NO 19
<211> LENGTH: 396
<212> TYPE: DNA
<213> ORGANISM: Mus musculus

<400> SEQUENCE: 19
atgaaatgca gctgggttat cttcttcctg atggcagtgg ttacaggggt cgatgcagag      60
gttcacctgc agcagtctgg ggcagagctt gtgaagccag ggcctcagt caagttgtcc     120 tgcacagcct ctggcttcag tattagagac acctatatgc actgggtgag gcagaggcct    180
gaacagggcc tggaatggat tacagggatt gatcctgaaa atggtaattc taaatatgcc    240
ccgaggttcc aggacaaggc cactataata gcagacacgt cctccaacac agttcacctg    300
cagctcgaca ccctgacatc tgaggacact gccgtctatt attgtactag ggagcttgct    360
tactgggccc aagggactcg ggtcactgtc tctgca                              396

<210> SEQ ID NO 20
<211> LENGTH: 396
<212> TYPE: DNA
<213> ORGANISM: Mus musculus

<400> SEQUENCE: 20
atgatgagtc ctgcccagtt cctgtttctg ttagtgctct ggattcggga gaacaacggt      60
gatgttgtga tgacccagat tccactcact tgtcgcttaa ccattggaca accagcctcc     120
atctcttgca gtcaagtca gagtctctta catcgtgatg aaagacata tttgaattgg      180 ttgttacaga ggccaggcca gtctccaaag cgcctaatgt atctggtgtc taaactggac    240
tctggagtcc ctgataggtt cactggcagt ggatcaggga cagagttcac actgaaaatc    300
agcagagtgg aggctgaaga tttgggagtt tattattgct ggcaaggtac acatttttcct   360 cggacgttcg gtggaggcac caagctggaa atcaaa                              396

```
<210> SEQ ID NO 21
<211> LENGTH: 112
<212> TYPE: PRT
<213> ORGANISM: Mus musculus

<400> SEQUENCE: 21

Asp Val Val Leu Thr Gln Thr Pro Leu Asn Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Met Tyr Leu Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 22
<211> LENGTH: 113
<212> TYPE: PRT
<213> ORGANISM: Mus musculus

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Tyr Ile Lys Asp Thr
            20                  25                  30

Tyr Ile His Trp Val Lys Gln Arg Pro Glu Glu Val Leu Glu Trp Ile
        35                  40                  45

Gly Gly Ile Asp Pro Ala Asp Gly Asp Thr Arg Tyr Asp Pro Lys Phe
    50                  55                  60

Gln Gly Lys Ala Thr Ile Thr Ala Asp Thr Ser Ser Asn Ser Ala Tyr
65                  70                  75                  80

Leu His Leu Thr Ser Leu Thr Ser Glu Asp Thr Ala Val Tyr Phe Cys
                85                  90                  95

Ala Arg Glu Leu Ala Tyr Trp Gly Gln Gly Thr Leu Val Thr Val Ser
            100                 105                 110

Ala

<210> SEQ ID NO 23
<211> LENGTH: 112
<212> TYPE: PRT
<213> ORGANISM: Mus musculus

<400> SEQUENCE: 23

Glu Ala Val Met Thr Gln Thr Pro Leu Thr Leu Ser Val Ile Ile Gly
1               5                   10                  15

Gln Pro Ala Ser Phe Ser Cys Lys Ser Ser His Ser Leu Leu His Arg
            20                  25                  30

Asp Gly Arg Thr Tyr Leu Asn Trp Leu Leu Gln Arg Pro Gly Gln Ser
        35                  40                  45

Pro Gln Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
```

```
               65                  70                  75                  80
Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 24
<211> LENGTH: 112
<212> TYPE: PRT
<213> ORGANISM: Mus musculus

<400> SEQUENCE: 24

Glu Val Gln Leu Gln Gln Ser Gly Ala Glu Phe Val Arg Pro Gly Ala
1               5                   10                  15

Ala Val Lys Leu Ser Cys Thr Val Ser Gly Leu Asn Ile Lys Asp Ser
            20                  25                  30

Tyr Leu His Trp Val Lys Gln Arg Pro Glu Gln Gly Leu Glu Trp Ile
        35                  40                  45

Gly Gly Ile Asp Pro Ala Asn Gly Asp Val Glu Tyr Asp Pro Lys Phe
    50                  55                  60

Gln Gly Lys Ala Ala Ile Thr Ala Asp Thr Ser Asn Thr Ala Tyr
65                  70                  75                  80

Leu Arg Leu Ser Ser Leu Thr Ser Glu Asp Thr Ala Val Tyr Tyr Cys
                85                  90                  95

Ala Pro Phe Pro Tyr Trp Gly Gln Gly Thr Leu Val Thr Val Ser Ala
            100                 105                 110

<210> SEQ ID NO 25
<211> LENGTH: 112
<212> TYPE: PRT
<213> ORGANISM: Mus musculus

<400> SEQUENCE: 25

Asp Ala Val Leu Thr Gln Thr Pro Leu Thr Leu Ser Val Thr Ile Gly
1               5                   10                  15

His Pro Ala Ser Ile Ser Cys Lys Ser Ser Gln Ser Leu Leu His Arg
            20                  25                  30

Asp Gly Lys Thr Tyr Leu Asn Trp Val Phe Gln Arg Pro Gly Gln Ser
        35                  40                  45

Pro Gln Arg Leu Ile Tyr Leu Val Ser Leu Val Asp Ser Gly Val Pro
    50                  55                  60

Asp Arg Phe Thr Gly Ser Gly Ser Gly Thr Asp Phe Thr Leu Lys Ile
65                  70                  75                  80

Asn Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 26
<211> LENGTH: 116
<212> TYPE: PRT
<213> ORGANISM: Mus musculus

<400> SEQUENCE: 26

Gly Val Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Lys Asp Thr
            20                  25                  30
```

```
Tyr Met His Trp Val Lys Gln Arg Pro Glu Gln Gly Leu Glu Trp Ile
         35                  40                  45

Gly Gly Ile Asp Pro Glu Asn Gly Asn Thr Lys Phe Asp Pro Arg Phe
 50                  55                  60

Gln Asp Lys Ala Thr Ile Thr Ala Asp Thr Ser Ser Asn Thr Val Leu
 65                  70                  75                  80

Leu Gln Leu Ser Ser Leu Thr Ser Glu Asp Thr Ala Val Tyr Tyr Cys
                 85                  90                  95

Ala Asn Leu Gly Arg Pro Phe Ala His Trp Gly Gln Gly Thr Leu Val
                100                 105                 110

Thr Val Ser Ala
        115

<210> SEQ ID NO 27
<211> LENGTH: 112
<212> TYPE: PRT
<213> ORGANISM: Mus musculus

<400> SEQUENCE: 27

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                 20                  25                  30

Arg Thr Arg Lys Asn Tyr Leu Ala Trp Tyr Gln Gln Lys Leu Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Phe Ile Thr Phe Gly Ala Gly Thr Lys Leu Glu Leu Lys
                100                 105                 110

<210> SEQ ID NO 28
<211> LENGTH: 123
<212> TYPE: PRT
<213> ORGANISM: Mus musculus

<400> SEQUENCE: 28

Glu Val Gln Leu Gln Gln Ser Gly Pro Asp Leu Val Lys Pro Gly Ala
 1               5                  10                  15

Ser Val Lys Val Ser Cys Lys Ala Ser Gly Tyr Thr Phe Thr Val Tyr
                 20                  25                  30

Val Ile His Trp Val Ile Gln Lys Pro Gly Gln Gly Leu Glu Trp Ile
             35                  40                  45

Gly Tyr Ile Asn Pro Tyr Asn Asp Gly Ala Glu Tyr Asn Glu Asn Phe
 50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Thr Arg Gly Glu Asn Tyr Tyr Ser Arg Tyr Gly Phe Phe Asp Val
                100                 105                 110

Trp Gly Ala Gly Thr Thr Val Thr Val Ser Ser
        115                 120
```

<210> SEQ ID NO 29
<211> LENGTH: 219
<212> TYPE: PRT
<213> ORGANISM: Artificial Sequence
<220> FEATURE:
<223> OTHER INFORMATION: chimeric antibody light chain

<400> SEQUENCE: 29

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Phe Leu Ile Tyr Lys Ala Ser Asn Arg Phe Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 30
<211> LENGTH: 443
<212> TYPE: PRT
<213> ORGANISM: Artificial Sequence
<220> FEATURE:
<223> OTHER INFORMATION: chimeric antibody heavy chain

<400> SEQUENCE: 30

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Gly Ile Asp Pro Ala Asp Gly Glu Thr Lys Tyr Asp Pro Lys Phe
    50                  55                  60

Gln Asp Lys Ala Thr Ile Thr Thr Asp Thr Ser Ser Asn Thr Val Tyr
65                  70                  75                  80

Leu Gln Ile Ser Ser Leu Thr Ser Glu Asp Thr Ala Val Tyr Tyr Cys
                85                  90                  95

Val Arg Ser Phe Asp Tyr Trp Gly Gln Gly Thr Thr Leu Thr Val Ser
```

```
                         100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
        130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Arg Val Glu Pro Lys Ser Cys Asp Lys Thr His Thr Cys Pro Pro
    210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 31
<211> LENGTH: 11
<212> TYPE: PRT
<213> ORGANISM: Artificial Sequence
<220> FEATURE:
<223> OTHER INFORMATION: amino acids 490-500 of prostate specific
      membrane antigen

<400> SEQUENCE: 31

Gly Lys Ser Leu Tyr Glu Ser Trp Thr Lys Lys
1               5                   10
```

ANTIBODIES AGAINST PROSTATE SPECIFIC MEMBRANE ANTIGEN

This patent application is a national stage filing under 35 U.S.C. §371 of International Application No. PCT/CA2010/000567, filed on Apr. 10, 2010 which claims priority to U.S. Provisional Patent Application No. 61/202,867, filed on Apr. 14, 2009 and U.S. Provisional Patent Application No. 61/249,094, filed on Oct. 6, 2009, the entire contents of each application are incorporated herein by reference.

FIELD OF INVENTION

The present invention relates to the field of antibodies (Ab) and to antigen binding fragments thereof. More specifically, the invention relates to diagnostic and therapeutic antibodies and antigen binding fragments capable of binding to prostate specific membrane antigen (PSMA).

BACKGROUND OF INVENTION

Prostate cancer is the most commonly diagnosed nonskin malignancy in males from developed countries. It is estimated that one in six males will be diagnosed with prostate cancer (PCa) in their lifetime. The diagnosis of PCa has greatly improved following the use of serum-based markers such as the prostate-specific antigen (PSA). However, the use of tumor-associated markers offers alternative strategies in disease management and may prove useful for in vivo tumor imaging purposes and further development of targeted therapies.

Identification of the prostate specific membrane antigen (PSMA) marker, a tumor associated marker, has generated interest for both applications. PSMA is a glycoprotein highly restricted to prostate secretory epithelial cell membranes. Its expression has been correlated with tumor aggressiveness. Various immunohistological studies have demonstrated increased PSMA levels in virtually all cases of prostatic carcinoma compared to those levels in benign prostate epithelial cells. Intense PSMA staining is found in all stages of the disease, including prostatic intraepithelial neoplasia, late stage androgen-independent prostate cancer and secondary prostate tumors localized to lymph nodes, bone, soft tissue, and lungs. PSMA was originally identified as the molecule recognized by 7E11, a monoclonal antibody (MAb) reactive to the prostate cancer cell line LNCaP. It was subsequently cloned from these cells as a 2.65 kb cDNA encoding a 750 amino acid cell surface type II integral membrane glycoprotein of 100 kDa. PSMA forms a noncovalent homodimer that possesses glutamate carboxypeptidase activity based on its ability to process the neuropeptide N-acetylaspartyl-glutamate and glutamate-conjugated folate derivatives. Although the precise biological role played by PSMA in disease pathogenesis remains elusive, its overexpression in PCa might potentially be associated with the growth balance of the prostate gland. Indeed, recent evidence suggests that PSMA performs multiple physiological functions related to cell survival and migration.

Antibody-based therapeutics have emerged as important components of therapies for an increasing number of human malignancies in such fields as oncology, inflammatory and infectious diseases. In most cases, the basis of the therapeutic function is the high degree of specificity and affinity the antibody-based drug has for its target antigen. Arming monoclonal antibodies with drugs, toxins, or radionuclides is yet another strategy by which mAbs may induce therapeutic effect. By combining the exquisite targeting specificity of antibody with the tumor killing power of toxic effector molecules, immunoconjugates permit sensitive discrimination between target and normal tissue thereby resulting in fewer side effects than most conventional chemotherapeutic drugs.

Given the physical properties of PSMA and its expression pattern in relation to disease progression, its large extracellular domain provides an excellent target in the development of ligands for diagnostic and therapeutic intervention. The first PSMA-specific MAb reported, 7E11, was subsequently developed and commercialized as a diagnostic agent for tumor imaging (ProstaScint, Cytogen, Princeton, N.J.). However, this antibody recognizes an intracellular epitope of PSMA which limits its usefulness as an imaging agent for the detection of PSMA. More recently, MAbs such as J591 that recognize the extracellular portion of PSMA were developed, however such antibodies have uncharacterized epitope specificities. The development of anti-PSMA antibodies with diagnostic and/or therapeutic activity is needed. The present invention seeks to meet these and other needs.

SUMMARY OF THE INVENTION

The present invention relates to antibodies and antigen binding fragments, cells comprising or expressing these antibodies or antigen binding fragments as well as kits useful for the treatment, detection of tumor cells or tumor neovasculature or in the diagnosis of cancer.

The Applicant came to the unexpected discovery that the antibodies and antigen binding fragments of the present invention do not need to be conjugated with a toxic or other therapeutic moiety in order to efficiently reduce the growth of cancer cells in vivo. In fact, these antibodies or antigen binding fragments are capable of inducing or promoting cell death of PSMA-expressing cells (especially PSMA-expressing tumor cells) by themselves. This represents a significant advantage over other antibodies known in the art.

The antibodies and antigen binding fragments of the present invention are particularly useful for reducing or inhibiting the growth of tumor cells. More particularly, these antibodies or antigen binding fragments may, for example, be effective at reducing tumor growth at a dose of about 10 mg/kg (e.g. less than 30 mg/kg), although other dosages are encompassed by the present invention, (e.g., 1 to 30 mg/kg or more, 1 to 29 mg/kg, 1 to 25 mg/kg, 1 to 20 mg/kg, 5 to 20 mg/kg, 5 to 29 mg/kg, 5 to 15 mg/kg, 5 to 10 mg/kg and any ranges in between those mentioned herein). The antibodies and antigen binding fragments of the present invention may also be linked to a detectable moiety for detection and/or diagnostic purposes. Optionally, if so desired, these antibodies and antigen binding fragments may be linked to or co-administered with a therapeutic moiety. In an aspect of the invention, for therapeutic purposes, the naked antibody or antigen binding fragments may be unconjugated.

The present invention provides in one aspect thereof, an isolated or substantially purified antibody or antigen binding fragment which may be capable of specific binding to PSMA (Gene bank accession No. AAA60209.1). Since, the antibody or antigen binding fragment of the present invention may advantageously promote cell death independently of the presence of a cytotoxic molecule, they are referred herein as naked antibodies or antigen binding fragments thereof.

More specifically and in accordance with an embodiment of the invention, the antibody or antigen binding fragment may bind to a domain located between amino acids 490 and 500 of PSMA.

In accordance with another embodiment of the invention, the antibody or antigen binding fragment may be capable of binding to an epitope comprised within amino acid 490 and 500 of PSMA. In fact, the antibody or antigen binding fragment may be capable of binding to an epitope consisting of amino acids 490 to 500 (inclusively) of PSMA, i.e., (Gly Lys Ser Leu Tyr Glu Ser Trp Thr Lys Lys (SEQ ID NO.:31)).

Also encompassed by the present invention are antibodies or antigen binding fragments having the same epitope specificity as the antibody of the present invention and having substantially the same activity, or preferably substantially the same therapeutic activity. A candidate antibody may be identified by determining whether it will bind to the epitope to which the antibodies described herein binds and/or by performing competition assays with antibodies or antigen binding fragments known to bind to the epitope. A candidate antibody is preferably selected for its ability to reduce the growth of cancer cells without being conjugated to a toxin or to other therapeutic moiety.

Therefore another aspect the present invention provides an isolated naked antibody or antigen binding fragment capable of competing with the antibody or antigen binding fragment described herein.

In further aspects, the present invention provides method of treatment and method of detection using the antibody or antigen binding fragment of the present invention.

The term "antibody" refers to intact antibody, monoclonal or polyclonal antibodies. The term "antibody" also encompasses, multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen. It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR), e.g., $V_H$ CDR3 comprising or not additional sequence (linker, framework region(s) etc.) and (v) a combination of two to six isolated CDRs comprising or not additional sequence (linker, framework region(s) etc.). Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

In fact, because CDR sequences are responsible for most antibody-antigen interactions, it is possible to express recombinant antibodies that shows the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized to create an entirely synthetic variable region clone. This process has certain advantages such as elimination or inclusion of particular restriction sites, or optimization of particular codons.

Of course, the totality or portions of the framework region of the antibody described herein may be used in conjunction with the CDRs in order to optimize the affinity, specificity or any other desired properties of the antibody.

The term "naked antibody or antigen binding fragment" refers to an antibody or antigen binding fragment which has the ability to induce cell death in vitro or in vivo, without needed to be conjugated with a toxin, drug or the like. The term "naked", in some instances may also refer to an antibody or antigen binding fragment which is optionally conjugated with a moiety which is considered as being therapeutic.

Antibodies and/or antigen binding fragments of the present invention may originate, for example, from a mouse, a rat or any other mammal or from other sources such as through recombinant DNA technologies.

BRIEF DESCRIPTION OF THE DRAWINGS

In the appended drawings which illustrates non-limitative, exemplary embodiments of the present invention:

FIG. 1 shows the sequence of the heavy and light variable region of the murine monoclonal anti-PSMA antibody (mAb1) of the present invention where the predicted CDRs correspond to bold letters;

FIG. 2: shows the sequence of the heavy and light variable region of a further murine monoclonal anti-PSMA antibody (mAb2) of the present invention where the predicted CDRs correspond to bold letters;

FIG. 3: shows the sequence of the heavy and light variable region of yet additional murine monoclonal anti-PSMA antibodies of the present invention where the predicted CDRs correspond to bold letters;

FIG. 10: Amino acid sequence of the light (SEQ ID NO.: 29) and heavy chain (SEQ ID NO.:30) of a murine/human chimeric antibody (chAb1). Characters underlined represent the human-derived sequence and the others, the murine;

FIG. 11A: Immunoreactivity of chAb1 to LNCaP or PC3 cancer cell lines. Serially diluted purified chimeric antibody was tested by ELISA on a cell membrane preparation that express PSMA (LNCaP) or not (PC-3).

FIG. 11B: Immunoreactivity of a further chimeric Ab (chAb3) to LNCaP or PC3 cancer cell lines. The antibodies react strongly with the LNCaP preparation while the PC-3 remains unreactive;

DETAILED DESCRIPTION OF THE INVENTION

Figure 4:
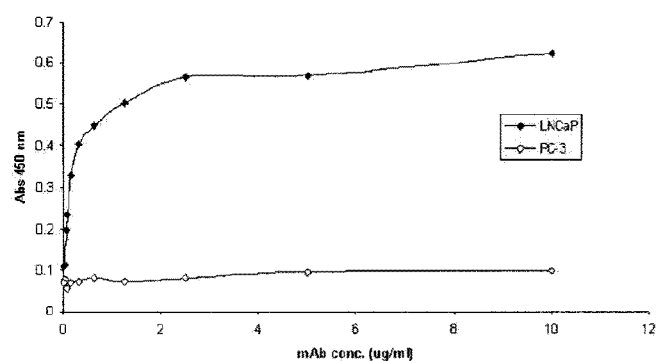
FIG. 4: immunoreactivity mAb1 to cancer cell line. Serially diluted purified antibody was tested by ELISA on a cell membrane preparation that express PSMA (LNCaP) or not (PC-3). The antibody reacts strongly with the LNCaP preparation while the PC-3 remains unreactive.

The present description refers to a number of documents, the content of which is herein incorporated by reference in their entirety.

In order to provide a clear and consistent understanding of the terms used in the present disclosure, a number of definitions are provided below. Moreover, unless defined otherwise, all technical and scientific terms as used herein have the same meaning as commonly understood to one of ordinary skill in the art to which this invention pertains.

The present invention relates in one aspect thereof to isolated antibodies or antigen binding fragments capable of binding to prostate specific membrane antigen (PSMA). More particularly, the present invention relates to diagnostic and/or therapeutic antibodies or antigen binding fragments having specificity for PSMA.

The binding site of an antibody has mainly been attributed to the complementarity-determining regions (CDRs). In some instances, a single CDR (e.g., V$_H$ CDR3) may be sufficient to provide antigen recognition and specificity of the antibody. The polypeptide, antibody or antigen-binding fragment of the present invention may preferably comprise the heavy and light chain CDR3s of the antibodies listed in FIG. 1. The polypeptide, antibody or antigen-binding fragment may further comprise the CDR2s of the antibodies listed in FIG. 1. The polypeptide, antibody or antigen-binding fragment may also comprise the CDR1s of the antibodies listed in FIG. 1. The polypeptide, antibody or antigen-binding fragment may further comprise any combinations of the CDRs.

CDRs may be identified by analyzing the amino acid sequence and/or structure of the variable domain of an antibody. Computer-implemented analysis and modeling of antigen-binding site are based on homology analysis comparing the target antibody sequence with those of antibodies with known structures or structural motifs in existing data bases. By using such homology-based modeling methods approximate three-dimensional structure of the target antibody is constructed (Kabat and Wu (1972) Proc. Natl. Acad. Sci. USA 69: 960 964). More recently, the canonical loop concept has been incorporated into the computer-implemented structural modeling of an antibody combining site (Chothia et al. (1989) Nature (London) 342:877; Chothia and Lesk JMB 196:901 (1987)). It is also possible to improve the modeling of CDRs of antibody structures by combining the homology-based modeling with conformational search procedures (Martin, A. C. R. (1989) PNAS 86: 9268-72). Antibody modeling software are also available for determining the CDRs (AbM: Accelrys, Cambridge, U.K.)

Antibodies and Antigen Binding Fragments that Binds to PSMA

The variable regions described herein may be fused with constant regions of a desired species thereby allowing recognition of the antibody by effector cells of the desired species. The constant region may originate, for example, from an IgG1, IgG2, IgG3, or IgG4 subtype. In an embodiment of the invention, the constant region may be of human origin. In another embodiment of the invention, the constant region may be of murine origin. Cloning or synthesizing a constant region in frame with a variable region is well within the scope of a person of skill in the art and may be performed, for example, by recombinant DNA technology.

In certain embodiments of the present invention, antibodies that bind to PSMA may be of the IgG1, IgG2, IgG3, or IgG4 subtype. More specific embodiments of the invention relates to an antibody of the IgG1 subtype. In another specific embodiment of the invention relates to an antibody of the IgG2 subtype. In yet another specific embodiment of the invention relates to an antibody of the IgG3 subtype. The antibody may be a humanized antibody of the IgG1 subtype that is biologically active in mediating antibody-dependent cellular cytotoxicity (ADCC), complement-mediated cytotoxicity (CMC), or associated with immune complexes. The typical ADCC involves activation of natural killer (NK) cells and is reliant on the recognition of antibody-coated cells by Fc receptors on the surface of the NK cells. The Fc receptors recognize the Fc domain of antibodies such as is present on IgG1, which bind to the surface of a target cell, in particular a cancerous cell that expresses an antigen, such as PSMA. Once bound to the Fc receptor of IgG the NK cell releases cytokines and cytotoxic granules that enter the target cell and promote cell death by triggering apoptosis.

The present invention described a collection of antibodies that bind to PSMA. In certain embodiments, the antibodies may be selected from the group consisting of polyclonal antibodies, monoclonal antibodies such as chimeric or humanized antibodies, antibody fragments such as antigen binding fragments, single chain antibodies, deimmunized antibodies, human antibodies, recombinant antibodies, domain antibodies, and polypeptides with an antigen binding region.

The present invention therefore provides in another aspect thereof, an isolated antibody or antigen binding fragment comprising a light chain variable domain having;
  a. a CDRL1 sequence comprising SEQ ID NO:8 or a variant having one, two, three or four amino acid variations selected from the group consisting of amino acid substitutions, deletions, insertions or combination thereof in SEQ ID NO:8;
  b. a CDRL2 sequence comprising SEQ ID NO:9 or a variant having one, two, three or four amino acid variations selected from the group consisting of amino acid substitutions, deletions, insertions or combination thereof in SEQ ID NO:9, and/or;
  c. a CDRL3 sequence comprising SEQ ID NO:10 or a variant having one, two, three or four amino acid variations selected from the group consisting of amino acid substitutions, deletions, insertions or combination thereof in SEQ ID NO:10.

In accordance with the present invention, the antibody or antigen binding fragment of the present invention may have a framework region which may have, for example at least 70, 71, 72 etc. amino acids of the framework region of SEQ ID NO:4.

In accordance with an embodiment of the invention, the isolated antibody or antigen binding fragment may also comprise a complementary heavy chain variable domain.

The isolated antibody or antigen binding fragment may thus also comprise a heavy chain variable domain having;
  a. a CDRH1 sequence comprising SEQ ID NO:5 or a variant having one, two, three or four amino acid variations selected from the group consisting of amino acid substitutions, deletions, insertions or combination thereof in SEQ ID NO:5;
  b. a CDRH2 sequence comprising SEQ ID NO:6 or a variant having one, two, three or four amino acid variations selected from the group consisting of amino acid substitutions, deletions, insertions or combination thereof in SEQ ID NO:6, and/or;
  c. a CDRH3 sequence comprising SEQ ID NO:7 or a variant having one, two, three or four amino acid variations selected from the group consisting of amino acid substitutions, deletions, insertions or combination thereof in SEQ ID NO:7.

In accordance with the present invention, the antibody or antigen binding fragment of the present invention may have a framework region which may have, for example at least 59, 60, 61 etc. amino acids of the framework region of SEQ ID NO:2.

In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

Further in accordance with the present invention, the antibody or antigen binding fragment may comprise:
- a. At least two CDRs of a CDRL1, CDRL2 or CDRL3 and;
- b. At least two CDRs of a CDRH1, one CDRH2 or one CDRH3.

An exemplary combination of CDRs may be those which are part of the same variable region illustrated in FIG. 1.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

The antibody or antigen binding fragment may also more preferably comprise one CDRL1, one CDRL2 and one CDRL3 and one CDRH1, one CDRH2 and one CDRH3.

As indicated above, antibodies or antigen binding fragment having CDR variants are encompassed by the present invention. In a particular embodiment, antibodies comprising a variant CDR may have one or two amino acid variations in comparison with the CDR sequence presented in SEQ ID NOs: 5 to 10. An antibody or antigen binding fragment containing two to six CDRs, may also have several variations in the CDRs in comparison with those presented in SEQ ID NO:5 to 10. For example, each of the CDR may have one or two amino acid variations. In particular embodiment only one of the CDR has one or two amino acid variations. In another embodiment, only two CDRs have one or two amino acid variations. In yet another embodiment only four of the CDRs have one or two amino acid variations. In another embodiment only five of the CDRs have one or two amino acid variations. Such variation may be a conservative or a non conservative amino acid substitution.

In another aspect the present invention relates to a polypeptide or an antibody comprising (on a single polypeptide chain or on separate polypeptide chains) at least one complementarity-determining region of a light chain variable domain and at least one complementarity-determining region of a heavy chain variable domain of the antibody described herein.

In another aspect the present invention provides an isolated antibody or antigen binding fragment comprising a heavy chain variable domain having;
- a. a CDRH1 sequence comprising SEQ ID NO:5 or a variant having one, two, three or four amino acid variations selected from the group consisting of amino acid substitutions, deletions, insertions or combination thereof in SEQ ID NO:5;
- b. a CDRH2 sequence comprising SEQ ID NO:6 or a variant having one, two, three or four amino acid variations selected from the group consisting of amino acid substitutions, deletions, insertions or combination thereof in SEQ ID NO:6, and/or;
- c. a CDRH3 sequence comprising SEQ ID NO:7 or a variant having one, two, three or four amino acid variations selected from the group consisting of amino acid substitutions, deletions, insertions or combination thereof in SEQ ID NO:7.

In accordance with the present invention, the antibody or antigen binding fragment of the present invention may have a framework region which may have, for example at least 59, 60, 61 etc. amino acids of the framework region of SEQ ID NO:2.

The present invention also provides an isolated antibody or antigen binding fragment comprising a light chain variable domain having;
- a) a CDRL1 sequence which may comprise SEQ ID NO:16 or a variant having one, two, three or four amino acid variations selected from the group consisting of amino acid substitutions, deletions, insertions and combination thereof in SEQ ID NO:16;
- b) a CDRL2 sequence which may comprise SEQ ID NO:17 or a variant having one, two, three or four amino acid variations selected from the group consisting of amino acid substitutions, deletions, insertions and combination thereof in SEQ ID NO:17, and/or;
- c) a CDRL3 sequence which may comprise SEQ ID NO:18 or a variant having one, two, three or four amino acid variations selected from the group consisting of amino acid substitutions, deletions, insertions and combination thereof in SEQ ID NO:18.

In accordance with the present invention, the isolated antibody or antigen binding fragment may comprise a light chain framework region having at least 59 (e.g., 59, 60, 61, 62, 63, 64, 65 etc.) consecutive amino acids of the light chain framework region of SEQ ID NO:12.

Further in accordance with the present invention, the isolated antibody or antigen binding may further comprise a heavy chain variable domain having;
- a) a CDRH1 sequence which may comprise SEQ ID NO:13 or a variant having one, two, three or four amino acid variations selected from the group consisting of amino acid substitutions, deletions, insertions and combination thereof in SEQ ID NO:13;
- b) a CDRH2 sequence which may comprise SEQ ID NO:14 or a variant having one, two, three or four amino acid variations selected from the group consisting of amino acid substitutions, deletions, insertions and combination thereof in SEQ ID NO:14, and/or;
- c) a CDRH3 sequence which may comprise SEQ ID NO:15 or a variant having one, two, three or four amino acid variations selected from the group consisting of amino acid substitutions, deletions, insertions and combination thereof in SEQ ID NO:15.

The isolated antibody or antigen binding fragment may comprise a heavy chain framework region having at least 70 (e.g., 70, 71, 72, 73, 74, 75, 76 etc.) consecutive amino acids of the heavy chain framework region of SEQ ID NO:11.

In one embodiment, the CDRL1 may be a CDRL1 variant comprising one amino acid substitution in SEQ ID NO.:16.

In a further embodiment, the antibody may comprise a heavy chain framework region which may be at least 75% identical to the heavy chain framework region of SEQ ID NO: 11.

In accordance with an embodiment of the invention, the isolated antibody or antigen binding fragment may also comprise a complementary light chain variable domain.

The antibody or antigen binding fragment of the present invention may be selected from the group consisting of:
- a) an antibody or antigen binding fragment which may comprise a light chain variable region as defined in SEQ ID NO.:4 and a complementary heavy chain variable region;
- b) an antibody or antigen binding fragment which may comprise a light chain variable region as defined in SEQ ID NO.:12 and a complementary heavy chain variable region;
- c) an antibody or antigen binding fragment which may comprise a light chain variable region as defined in SEQ ID NO.:21 and a complementary heavy chain variable region;

d) an antibody or antigen binding fragment which may comprise a light chain variable region as defined in SEQ ID NO.:23 and a complementary heavy chain variable region;
e) an antibody or antigen binding fragment which may comprise a light chain variable region as defined in SEQ ID NO.:25 and a complementary heavy chain variable region;
f) an antibody or antigen binding fragment which may comprise a light chain variable region as defined in SEQ ID NO.:27 and a complementary heavy chain variable region;
g) an antibody or antigen binding fragment which may comprise a heavy chain variable region as defined in SEQ ID NO.:2 and a complementary light chain variable region;
h) an antibody or antigen binding fragment which may comprise a heavy chain variable region as defined in SEQ ID NO.:11 and a complementary light chain variable region;
i) an antibody or antigen binding fragment which may comprise an heavy chain variable region as defined in SEQ ID NO.:22 and a complementary light chain variable region;
j) an antibody or antigen binding fragment which may comprise a heavy chain variable region as defined in SEQ ID NO.:24 and a complementary light chain variable region;
k) an antibody or antigen binding fragment which may comprise an heavy chain variable region as defined in SEQ ID NO.:26 and a complementary light chain, and;
l) an antibody or antigen binding fragment which may comprise a heavy chain variable region as defined in SEQ ID NO.:28 and a complementary light chain variable region.

In accordance with the present invention, the antibody or antigen binding fragment may comprise one CDRH1, one CDRH2 or one CDRH3.

In accordance with the present invention, the antibody or antigen binding fragment may also comprise one CDRH1, one CDRH2 and one CDRH3.

Again, variation in a single or several CDRs such as those mentioned above are encompassed by the present invention.

When only one of the light chain variable domain or the heavy chain variable domain is available, an antibody or antigen-binding fragment may be reconstituted by screening a library of complementary variable domains using methods known in the art (Portolano et al. The Journal of Immunology (1993) 150:880-887, Clarkson et al., Nature (1991) 352:624-628).

In an embodiment of the invention, the antibody or antigen binding fragment of the present invention may consist essentially of the six CDRs.

The present invention therefore encompasses an antibody or antigen binding fragment which comprises a CDRH1 as defined in SEQ ID NO.:5, a CDRH2 as defined in SEQ ID NO.:6, a CDRH3 as defined in SEQ ID NO.:7, a CDRL1 as defined in SEQ ID NO.:8, a CDRL2 as defined in SEQ ID NO.:9 and a CDRL3 as defined in SEQ ID NO.:10.

The present invention also encompasses an antibody or antigen binding fragment which is selected from the group consisting of:
an antibody or antigen binding fragment which may comprise the 3 CDRs of SEQ ID NO.:2 and the 3 CDRs of SEQ ID NO.:4;
an antibody or antigen binding fragment which may comprise the 3 CDRs of SEQ ID NO.:11 and the 3 CDRs of SEQ ID NO.:12;
an antibody or antigen binding fragment which may comprise the 3 CDRs of SEQ ID NO.:21 and the 3 CDRs of SEQ ID NO.:22;
an antibody or antigen binding fragment which may comprise the 3 CDRs of SEQ ID NO.:23 and the 3 CDRs of SEQ ID NO.:24;
an antibody or antigen binding fragment which may comprise the 3 CDRs of SEQ ID NO.:25 and the 3 CDRs of SEQ ID NO.:26, and;
an antibody or antigen binding fragment which may comprise the 3 CDRs of SEQ ID NO.:27 and the 3 CDRs of SEQ ID NO.:28.

The antibody or antigen binding fragment of the present invention therefore includes those comprising:
a) a light chain variable region as defined in SEQ ID NO.:4 and a heavy chain variable region as defined in SEQ ID NO.:2;
b) a light chain variable region as defined in SEQ ID NO.:12 and a heavy chain variable region as defined in SEQ ID NO.:11;
c) a light chain variable region as defined in SEQ ID NO.:21 and a heavy chain variable region as defined in SEQ ID NO.:22;
d) a light chain variable region as defined in SEQ ID NO.:23 and a heavy chain variable region as defined in SEQ ID NO.:24;
e) a light chain variable region as defined in SEQ ID NO.:25 and a heavy chain variable region as defined in SEQ ID NO.:26, or;
f) a light chain variable region as defined in SEQ ID NO.:27 and a heavy chain variable region as defined in SEQ ID NO.:28.

An antibody comprising a light chain as defined in SEQ ID NO.:29 and a heavy chain as defined in SEQ ID NO.:30 is also encompassed by the present invention.

In accordance with an embodiment of the invention, the antibody or antigen binding fragment may be stable at 37° C. Such stability may be observed for at least 3 months.

Also encompassed by the present invention, are polypeptides or antibodies comprising variable chains having at least one conservative amino acid substitution in at least one of the CDRs described herein.

Also encompassed by the present invention, are polypeptides or antibodies comprising variable chains having at least one conservative amino acid substitution in at least two of the CDRs.

Also encompassed by the present invention, are polypeptides or antibodies comprising variable chains having at least one conservative amino acid substitution in each of the 3 CDRs.

Also encompassed by the present invention, are polypeptides or antibodies comprising variable chains having at least two conservative amino acid substitutions in at least one of the CDRs and the other CDRs being as illustrated in FIG. 1 or having one or two conservative amino acid substitutions.

In another embodiment one or more of the CDRs of the present invention may comprise an amino acid insertion or deletion without affecting its activity. Such insertion or deletion may be found at one or both of the CDR's extremity or within the amino acid sequence of the CDR. Of course, combinations of insertion, deletion and/or substitution are also contemplated.

In another aspect, the present invention relates to a polypeptide, antibody or antigen binding fragment comprising (on a single polypeptide chain or on separate polypeptide chains) at least one complementarity-determining region of a light chain variable domain and at least one complementarity-determining region of a heavy chain variable domain of one of the antibodies or antigen binding fragment described herein.

The antibodies or antigen binding fragment of the present invention may further comprise additional amino acids flanking the amino and/or carboxy region of the CDR(s). Those additional amino acids may be random amino acid sequences, or may be obtained from antibody databases, they may be identical to the framework regions of the corresponding antibodies described herein or may include, for example, amino acid substitutions, insertion or deletion. Conservative amino acid substitution are particularly contemplated.

The antibody or antigen binding fragments may thus comprise one or more of the CDRs described herein and framework regions derived from those illustrated herein and being at least 75% identical.

Antibodies or antigen binding fragments that contain the light chain and heavy chain variable regions are also provided in the present invention. In accordance with an embodiment of the invention, the antibody or antigen binding fragment may contain two light chains variable regions and two heavy chains variable regions. Additionally, certain embodiments include antigen binding fragments, variants, and derivatives of these light and heavy chain variable regions.

Yet other exemplary embodiments of the invention includes an isolated antibody or antigen binding fragment capable of specific binding to PSMA or to a variant thereof, the antibody comprising:
  a. the light chain variable domain defined in SEQ ID NO.:4 or a variant having at least 75% amino acid identity (and up to 100% and any range therebetween) to SEQ ID NO:4; and
  b. the heavy chain variable domain defined in SEQ ID NO.:2 or a variant having at least 75% (and up to 100% and any range therebetween) amino acid identity to SEQ ID NO:2.

In accordance with the present invention, the light chain variant may comprise one, two, three or four amino acid variations selected from the group consisting of amino acid substitution, deletion or insertion in one, two or three CDR.

In accordance with the present invention, the substitution, insertion or deletion may be located preferably within the framework region. Alternatively, the substitution, insertion or deletion may be located within the one or more of the CDRs.

The present invention thus encompasses an antibody or antigen binding fragment having at least one (from 1 to 25 (and any range therebetween)) amino acid substitution, insertion or deletion in the framework region and at least one amino acid substitution, insertion or deletion in one or more of the CDRs.

It is to be understood herein, that the light chain variable region of the specific combination provided above may be changed for any other light chain variable region. Similarly, the heavy chain variable region of the specific combination provided above may be changed for any other heavy chain variable region.

Although preferred polypeptides or antibodies of the invention are those with CDRs which are 100% identical to those of the antibody described herein, the skilled artisan will know that variations in the amino acid sequence may be tolerated without loosing binding, specificity and/or affinity.

In an exemplary embodiment of the invention, the polypeptide or antibody may comprise an amino acid sequence which may be from 80 to 100% (including any individual percentage therebetween), 90 to 100%, or 95 to 100% (98% to 100%, 98.5% to 100%; 99% to 100%) identical to any one of SEQ ID NO.:3 to SEQ ID NO.:2 or 4 to 10.

As such, the variable regions that are contained in the anti-PSMA antibodies or antigen binding fragments may have 80%, 85%, 90%, 91%, 92%, 93%, 94%, 95%, 96%, 97%, 98%, 99% or 100% sequence identity to the variable regions presented in FIG. 1. Those skilled in the art will also recognize that the variants may include conservative amino acid changes, amino acid substitutions, deletions, or additions in the variable regions listed in FIG. 1.

Also, the CDRs that are contained in the anti-PSMA antibodies or antigen binding fragments may be variant CDRs with 80%, 85%, 90%, 91%, 92%, 93%, 94%, 95%, 96%, 97%, 98%, 99% or 100% sequence identity to the CDR sequences presented in FIG. 1. Those skilled in the art will also recognize that the variants may include conservative amino acid changes, amino acid substitutions, deletions, or additions in the CDR sequences listed in FIG. 1.

Other exemplary embodiments of the invention includes an isolated antibody or antigen binding fragment capable of specific binding to PSMA or to a variant thereof, the antibody comprising: the 3CDRs of a light chain variable domain defined in SEQ ID NO:4 and the 3CDRs of a heavy chain variable domain defined in SEQ ID NO:2.

Again, the light chain variable region of the specific combination provided above may be changed for any other light chain variable region described herein. Similarly, the heavy chain variable region of the specific combination provided above may be changed for any other heavy chain variable region described herein.

Variant Antibody and Antigen Binding Fragments

As indicated above, the present invention also encompasses variants of the antibodies or antigen binding fragments described herein. Variant antibodies or antigen binding fragments included are those having a variation in the amino acid sequence. For example, variant antibodies or antigen binding fragments included are those having at least one variant CDR (two, three, four, five or six variant CDRs), a variant light chain variable domain, a variant heavy chain variable domain, a variant light chain and/or a variant heavy chain. Variant antibodies or antigen binding fragments included in the present invention are those having, for example, similar or improved binding affinity in comparison with the original antibody or antigen binding fragment.

As used herein the term "variant" applies to any of the sequence described herein and includes for example, a variant CDR (either CDRL1, CDRL2, CDRL3, CDRH1, CDRH2 and/or CDRH3), a variant light chain variable domain, a variant heavy chain variable domain, a variant light chain, a variant heavy chain, a variant antibody, and a variant antigen binding fragment.

Variant antibodies or antigen binding fragments encompassed by the present invention are those which may comprise an insertion, a deletion or an amino acid substitution (conservative or non-conservative). These variants may have at least one amino acid residue in its amino acid sequence removed and a different residue inserted in its place.

The sites of greatest interest for substitutional mutagenesis include the hypervariable regions (CDRs), but modifications in the framework region or even in the constant region are also contemplated. Conservative substitutions may be made by exchanging an amino acid (of a CDR, variable chain, antibody, etc.) from one of the groups listed below (group 1 to 6) for another amino acid of the same group.

Other exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

As is known in the art, it may be of interest to modify the biological activity of a polypeptide by amino acid substitution, insertion or deletion. For example, modification of a polypeptide may result in an increase in the polypeptide's biological activity, may modulate its toxicity, may result in changes in bioavailability or in stability, or may modulate its immunological activity or immunological identity.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

| | |
|---|---|
| (group 1) | hydrophobic (aliphatic): norleucine, methionine (Met), Alanine (Ala), Valine (Val), Leucine (Leu), Isoleucine (Ile) |
| (group 2) | neutral hydrophilic: Cysteine (Cys), Serine (Ser), Threonine (Thr) |
| (group 3) | acidic: Aspartic acid (Asp), Glutamic acid (Glu) |
| (group 4) | basic: Asparagine (Asn), Glutamine (Gln), Histidine (His), Lysine (Lys), Arginine (Arg) |
| (group 5) | residues that influence chain orientation: Glycine (Gly), Proline (Pro); and |
| (group 6) | aromatic: Tryptophan (Trp), Tyrosine (Tyr), Phenylalanine (Phe) |

Non-conservative substitutions will entail exchanging a member of one of these classes for another.

Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable. It should be further noted that if the polypeptides are made synthetically, substitutions by amino acids, which are not naturally encoded by DNA (non-naturally occurring or unnatural amino acid) may also be made. A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide.

TABLE 1A

Amino acid substitution

| Original residue | Exemplary substitution | Exemplary conservative substitution |
|---|---|---|
| Ala (A) | Val, Leu, Ile, Gly, Ser | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala, Pro | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile, Tyr | Leu |
| Phe (F) | Met, Leu, Val, Ile, Ala, Tyr | Tyr, Leu |
| Pro (P) | Ala, Gly | Ala, Gly |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Polypeptides of the present invention may comprise for example, those containing amino acid sequences modified either by natural processes, such as posttranslational processing or by chemical modification techniques which are known in the art. Modifications may occur anywhere in a polypeptide including the polypeptide backbone, the amino acid side chains and the amino- or carboxy-terminus. A given polypeptide may contain many types of modifications. It is to be understood herein that more than one modification to the polypeptides described herein are encompassed by the present invention to the extent that the biological activity is substantially similar to the original polypeptide. Polypeptide modification may comprise, for example, amino acid insertion, deletion and substitution (i.e., replacement), either conservative or non-conservative (e.g., D-amino acids) in the polypeptide sequence where such changes do not substantially alter the overall biological activity of the polypeptide.

Variation in the amino acid sequence of the variant antibody or antigen binding fragment thus may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that the original antibody or antigen binding fragment amino acid sequence. The degree of similarity between two sequences is based upon the percentage of identities (identical amino acids) and of conservative substitution.

In addition, a non-naturally occurring amino acid may substitute for a naturally occurring amino acid (i.e., non-naturally occurring conservative amino acid substitution or a non-naturally occurring non-conservative amino acid substitution).

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174: 247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present invention therefore comprise those which may have at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

TABLE 1B

| | | Percent (%) sequence identity | | | | | | | | | | | | | | | | | | | | | | | | |
|---|---|---|---|---|---|---|---|---|---|---|---|---|---|---|---|---|---|---|---|---|---|---|---|---|---|---|
| | | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) sequence similarity | 75 | X | | | | | | | | | | | | | | | | | | | | | | | | | |
| | 76 | X | X | | | | | | | | | | | | | | | | | | | | | | | | |
| | 77 | X | X | X | | | | | | | | | | | | | | | | | | | | | | | |
| | 78 | X | X | X | X | | | | | | | | | | | | | | | | | | | | | | |
| | 79 | X | X | X | X | X | | | | | | | | | | | | | | | | | | | | | |
| | 80 | X | X | X | X | X | X | | | | | | | | | | | | | | | | | | | | |
| | 81 | X | X | X | X | X | X | X | | | | | | | | | | | | | | | | | | | |
| | 82 | X | X | X | X | X | X | X | X | | | | | | | | | | | | | | | | | | |
| | 83 | X | X | X | X | X | X | X | X | X | | | | | | | | | | | | | | | | | |
| | 84 | X | X | X | X | X | X | X | X | X | X | | | | | | | | | | | | | | | | |
| | 85 | X | X | X | X | X | X | X | X | X | X | X | | | | | | | | | | | | | | | |
| | 86 | X | X | X | XX | X | X | X | X | X | X | X | X | | | | | | | | | | | | | | |
| | 87 | X | X | X | X | X | X | X | X | X | X | X | X | X | | | | | | | | | | | | | |
| | 88 | X | X | X | X | X | X | X | X | X | X | X | X | X | X | | | | | | | | | | | | |
| | 89 | X | X | X | X | X | X | X | X | X | X | X | X | X | X | X | | | | | | | | | | | |
| | 90 | X | X | X | X | X | X | X | X | X | X | X | X | X | X | X | X | | | | | | | | | | |
| | 91 | X | X | X | X | X | X | X | X | X | X | X | X | X | X | X | X | X | | | | | | | | | |
| | 92 | X | X | X | X | X | X | X | X | X | X | X | X | X | X | X | X | X | X | | | | | | | | |
| | 93 | X | X | X | X | X | X | X | X | X | X | X | X | X | X | X | X | X | X | X | | | | | | | |
| | 94 | X | X | X | X | X | X | X | X | X | X | X | X | X | X | X | X | X | X | X | X | | | | | | |
| | 95 | X | X | X | X | X | X | X | X | X | X | X | X | X | X | X | X | X | X | X | X | X | | | | | |
| | 96 | X | X | X | X | X | X | X | X | X | X | X | X | X | X | X | X | X | X | X | X | X | X | | | | |
| | 97 | X | X | X | X | X | X | X | X | X | X | X | X | X | X | X | X | X | X | X | X | X | X | X | | | |
| | 98 | X | X | X | X | X | X | X | X | X | X | X | X | X | X | X | X | X | X | X | X | X | X | X | X | | |
| | 99 | X | X | X | X | X | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X | X | X | X | X | X |

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein The present invention encompasses CDRs, light chain variable domains, heavy chain variable domains, light chains, heavy chains, antibodies and/or antigen binding fragments which comprise at least 80% identity with the sequence described herein.

Production of the Antibodies in Cells

The antibodies that are disclosed herein can be made by a variety of methods familiar to those skilled in the art, such as hybridoma methodology or by recombinant DNA methods.

In another aspect, the present invention thus relates to an isolated cell that may produce the antibody or antigen binding fragment described herein. In accordance with the present invention, the isolated cell may be a hydridoma cell producing an antibody described herein. Alternatively, the isolated cell may be a hydridoma cell producing an antibody having the same epitope specificity as the antibody or antigen binding fragment described herein.

The present invention, therefore encompasses a cell (an isolated cell) which comprises and/or expresses an antibody or antigen binding fragment of the present invention or a portion thereof (e.g., such as during cloning procedures etc.). Although conventional hybridoma cells are contemplated, a person of skill in the art will readily know that other cells are suitable for expressing antibodies or antigen binding fragments, such as bacterial cells, yeast cells, mammalian expression system (e.g., CHO, 293 etc.). Cells that are particularly useful for expression of antibodies, are those which are able to suitably express the antibody (complete antibody, antibody chain(s) or fragments), suitably glycosylate it and/or suitably secrete it.

In an exemplary embodiment of the invention, the antibodies may be produced by the conventional hybridoma technology, where a mouse is immunized with an antigen, spleen cells isolated and fused with myeloma cells lacking HGPRT expression and hybrid cells selected by hypoxanthine, aminopterin and thymine (HAT) containing media.

In an additional exemplary embodiment of the invention, the antibodies may be produced by recombinant DNA methods.

In order to express the antibodies, nucleotide sequences able to encode any one of a light and heavy immunoglobulin chains described herein may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system respectively.

The term "vector" encompasses, without being limited to, autonomously replicating DNA or RNA molecule into which foreign DNA or RNA fragments may be inserted and then propagated in a host cell for expression and/or amplification of the foreign DNA or RNA molecule. A vector may comprise, without limitation, a linear plasmid and/or circular plasmid.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA (mRNA, siRNA, shRNA etc.) and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions, CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Antibody Conjugates

Although not necessary for therapeutic purposes, if desired, the antibody or antigen binding fragment of the present invention may nevertheless be conjugated with a therapeutic moiety. For detection purposes it may be particularly useful to conjugate the antibody or antigen binding fragment with a detectable moiety.

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, linked with DOTA) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}I$, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In an exemplary embodiment, the antibodies and antigen binding fragments may comprise a chemotherapeutic or cytotoxic agent. For example, the antibody and antigen binding fragments may be conjugated to the chemotherapeutic or cytotoxic agent. Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)). In other instances, the chemotherapeutic or cytotoxic agent may be comprised of, among others known to those skilled in the art, 5-fluorouracil, adriamycin, irinotecan, taxanes, pseudomonas endotoxin, ricin and other toxins.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the antibodies and antigen binding fragment are also encompassed by the present invention. The pharmaceutical composition may thus comprise an antibody or an antigen binding fragment and may also contain a pharmaceutically acceptable carrier.

In order to inhibit the growth of a tumor cell or in order to promote tumor cell death, the pharmaceutical composition may comprise a naked antibody or an antigen binding fragment and may also contain a pharmaceutically acceptable carrier. Of course, as indicated herein, it may be useful to also add a therapeutic moiety to the pharmaceutical composition (e.g., as a drug combination or conjugated to the antibody or antigen binding fragment described herein).

Yet other aspects of the invention relate to the use of the isolated antibody or antigen binding fragment described herein in the detection of tumor cells or in the diagnosis of cancer. Tumors cells which may be particularly detected are those which expresses PSMA, especially if PSMA is located at the cell surface. The antibody or antigen binding fragment of the present invention are particularly useful for the detection of prostate tumor cells or of other PSMA-expressing cells such as neovasculature (in the case of psoriasis) including tumor neovasculature.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally; intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. "Pharmaceutically acceptable carriers" thus may include, without limitation, diluents (such as phosphate buffered saline buffers, glycine buffer, water, saline), preservatives, solubilizers, emulsifiers, adjuvant and/ or carriers, dispersion media, coatings, antibacterial and antifungal agents, isotonic and absorption delaying agents and the like. The use of such media and agents is well known in the art. Except insofar as any conventional media or agent is incompatible with antibodies of the present invention, its use in pharmaceutical compositions is contemplated.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, rats, mouse and humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The present invention also relates to non-pharmaceutical composition which may contain the antibody or antigen binding fragment in aqueous solution or in other forms (e.g., freeze-dried, etc.). These non-pharmaceutical compositions may have utility in in vitro assays or the like.

In a further aspect the present invention relates to a formulation comprising the antibody or antigen binding fragment described herein and a glycine buffer. The pH of the formulation may be between 7.0 to 8.0. In accordance with a more specific embodiment of the invention, the pH of the formulation may be around 7.4.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The antibodies and antigen binding fragments may have therapeutic uses in the treatment of various diseases involving PSMA, such as prostate cancer. In an exemplary embodiment, the antibodies or antigen binding fragments may interact with cancer cells that express PSMA and induce an immunological reaction by mediating cellular immunity, humoral immunity or complement-mediated immunity. In other instances, the antibodies and fragments may block the interaction of PSMA with its protein partners.

In certain instances, the antibodies and antigen binding fragments therein may be administered concurrently in combination with other treatments given for the same condition. As such, the antibodies may be administered with anti-mitotics (eg., taxanes), platinum-based agents (eg., cisplatin), DNA damaging agents (eg. Doxorubicin), and other anti-cancer therapies that are known to those skilled in the art. In other instances, the antibodies and antigen binding fragments therein may be administered with other therapeutic antibodies.

The present invention relates in a further aspect thereof to a method for inhibiting the growth of a PSMA-expressing cell, the method may comprise contacting the cell with an effective amount of the antibody or antigen binding fragment described herein. The use of a naked anti-PSMA antibody is especially contemplated herein.

The present invention also encompasses method of treating cancer or inhibiting the growth of a PSMA expressing cells in a mammal, the method may comprise administering the antibody or antigen binding fragment described herein to a mammal in need. The use of a naked anti-PSMA antibody is also especially contemplated herein.

It is to be understood herein that by "inhibiting" it is meant a process by which the growth of a PSMA-expressing cell may be reduced, delayed, prevented and/or impaired. The term "inhibiting" may also encompass cell death.

As it will become apparent from the method described herein and in accordance with the present invention, the method may be performed using a naked antibody or antigen binding fragment described herein. The method may also be performed using the naked antibody either alone or in combination with a second therapeutic molecule. Furthermore, the method of the present invention may be carried out by using an antibody or antigen binding fragment which carries a diagnostic or therapeutic moiety.

In exemplary embodiment of the invention the method may be carried out using antibodies which may comprise a portion capable of attracting immune effector cells (e.g. natural killer cells, macrophages, etc.). Such portion may be a Fc region derived from the same species or from another species, e.g. a mice antibody Fc region, a human antibody Fc region, etc.

The present invention relates in an additional aspect thereof to a method for treating cancer, which may comprise administering to a subject in need an effective amount of a pharmaceutical composition that may comprise the antibody or antigen binding fragment described herein.

According to the present invention, a "subject" may be a mammal. In accordance with the present invention, the mammal may be a human being. A subject in need thereof encompasses a subject that may need PSMA expressing-cell detection and/or a subject that may need cancer treatment (such as prostate cancer).

The term "cancer" is intended to mean any cellular malignancy whose unique trait is the loss of normal controls which may result in unregulated growth, lack of differentiation and/or ability to invade local tissues and metastasize. Cancer may develop in any tissue of any organ. In a non-limitative embodiment of the present invention, cancer is intended to include prostate cancer.

The present invention also encompasses method of detecting cancer or detecting a PSMA-expressing cells in a mammal, the method may comprise administering the antibody or antigen binding fragment described herein to a mammal in need.

According to the present invention, contacting and/or detecting may occur in vivo, ex vivo or in vitro. In vivo contacting involves administering to a subject an antibody (effective amount thereof) of the invention, for example in a composition and/or pharmaceutical composition. Ex vivo contact and/or in vitro contact involves contact with a biological sample obtained from a subject. A biological sample may comprise a sample of blood, serum and/or tissue biopsies.

It is to be understood herein that the PSMA expressing cell may be a normal cell or a cell which aberrantly expresses PSMA (e.g., a tumor cell). A PSMA-expressing cell may also include neovasculature (non-tumor, e.g., psoriasis) and including tumor neovasculature. Such tumor neovasculature is not only found in prostatic cancer but also in bladder and lung tumors and also in breast tumor, colon tumor and pancreatic tumor.

According to the present invention, a cell which aberrantly expresses PSMA may be a cell that simply overexpresses PSMA without being tumoral. Alternatively and in accordance with the present invention, cell which aberrantly expresses PSMA may be a tumor cell.

In accordance with the present invention, a tumor cell may be a prostate cancer cell, an astrocytoma cell, a breast carcinoma cell, a carcinoid cell, a gastric carcinoma cell, a hepatocarcinoma cell, a Hodgkin's lymphoma cell, a leiomyoma cell, a lung adenocarcinoma cell, a lymphoma cell, a melanoma cell, an ovarian carcinoma cell, a rhabdosarcoma cell and/or a thyroid carcinoma cell. In an embodiment of the present invention, a tumor cell is a prostate cancer cell. In another embodiment, the prostate cancer cell may be a metastatic prostate cancer cell.

The present invention relates in another aspect thereof to a method for detecting a PSMA-expressing cell, the method may comprise contacting the cell with an antibody or antigen binding fragment described herein and detecting a complex formed by the antibody and the PSMA-expressing cell.

Another aspect of the invention relates to a method for detecting PSMA, or a variant having at least 80% sequence identity with PSMA, the method may comprise contacting a cell or a sample (biopsy, serum, plasma, urine etc.) comprising or suspected of comprising PSMA or the PSMA variant with the antibody or antigen binding fragments described herein and measuring binding.

The sample may originate from a mammal (e.g., a human) which may have cancer (e.g., prostate cancer) or may be suspected of having cancer (e.g., prostate cancer). The sample may be a tissue sample obtained from the mammal or a cell culture supernatant.

In accordance with the invention the sample may be a biopsy, a serum sample, a plasma sample, a blood sample or ascitic fluid obtained from the mammal. The antibody or antigen binding fragment described herein may advantageously detect PSMA.

The method may comprise quantifying the complex formed by the antibody or antigen binding fragment bound to PSMA or to the PSMA variant.

The antibody or antigen binding fragment of the present invention may more particularly be used in the detection, diagnosis or treatment of prostate cancer.

Additional aspects of the invention relates to kits which may include one or more container containing one or more antibodies or antigen binding fragments described herein.

Kits of the present invention may additionally include, if desired, one or many conventional components, for example, containers that may comprise one or many excipients and/or pharmaceutically acceptable vehicles, or any other additional containers that may be evident to a person skilled in the art. A kit according to the present invention may also advantageously include instructions in the form of a pamphlet or of any other support, indicating the quantities to be used and/or administered and/or the instructions to mix given components.

Nucleic Acids, Vectors and Cells

Antibodies are usually made in cells allowing expression of the light chain and heavy chain expressed from a vector(s) comprising a nucleic acid sequence encoding the light chain and heavy chain.

The present therefore encompasses nucleic acids capable of encoding any of the CDRs, light chain variable domains, heavy chain variable domains, light chains, heavy chains described herein.

Exemplary embodiments of nucleic acids of the present invention include nucleic acids encoding a light chain variable domain comprising:
  a. a CDRL1 sequence comprising SEQ ID NO:8 or a variant having one, two, three or four amino acid variations selected from the group consisting of amino acid substitutions, deletions, insertions and combination thereof in SEQ ID NO:8;
  b. a CDRL2 sequence comprising SEQ ID NO:9 or a variant having one, two, three or four amino acid variations selected from the group consisting of amino acid substitutions, deletions, insertions and combination thereof in SEQ ID NO:9, and/or;
  c. a CDRL3 sequence comprising SEQ ID NO:10 or a variant having one, two, three or four amino acid variations selected from the group consisting of amino acid substitutions, deletions, insertions and combination thereof in SEQ ID NO:10.

In accordance with the present invention, the nucleic acid may encode a light chain variable domain which may comprise at least two CDRs of a CDRL1, a CDRL2 or a CDRL3.

Also in accordance with the present invention, the nucleic acid may encode a light chain variable domain which may comprise one CDRL1, one CDRL2 and one CDRL3.

The present invention also relates to a nucleic acid encoding a heavy chain variable domain comprising:
a. a CDRH1 sequence comprising SEQ ID NO:5 or a variant having one, two, three or four amino acid variations selected from the group consisting of amino acid substitutions, deletions, insertions and combination thereof in SEQ ID NO:5;
b. a CDRH2 sequence comprising SEQ ID NO:6 or a variant having one, two, three or four amino acid variations selected from the group consisting of amino acid substitutions, deletions, insertions and combination thereof in SEQ ID NO:6, and/or;
c. a CDRH3 sequence comprising SEQ ID NO:7 or a variant having one, two, three or four amino acid variations selected from the group consisting of amino acid substitutions, deletions, insertions and combination thereof in SEQ ID NO:7.

In accordance with the present invention, the nucleic acid may encode a heavy chain variable domain which may comprise at least two CDRs of a CDRH1, a CDRH2 or a CDRH3.

In accordance with the present invention, the nucleic acid may encode a heavy chain variable domain which may comprise one CDRH1, one CDRH2 and one CDRH3.

Also encompassed by the present invention are nucleic acids encoding antibody variants having at least one conservative amino acid substitution.

In accordance with the present invention, the nucleic acid may encode a CDR comprising at least one conservative amino acid substitution.

In accordance with the present invention, the nucleic acid may encode a CDR comprising at least one conservative amino acid substitution in at least two of the CDRs.

In accordance with the present invention, the nucleic acid may encode a CDR comprising at least one conservative amino acid substitution in the 3 CDRs.

In accordance with the present invention, the nucleic acid may encode a CDR comprising at least two conservative amino acid substitutions in at least one of the CDRs.

In accordance with the present invention, the nucleic acid may encode a CDR comprising at least two conservative amino acid substitutions in at least two of the CDRs.

In accordance with the present invention, the nucleic acid may encode a CDR comprising at least two conservative amino acid substitutions in the 3 CDRs.

Other aspects of the invention relate to a nucleic acid encoding a light chain variable domain having at least 75% sequence identity (and up to 100% and any range therebetween) to a sequence selected from the group consisting of SEQ ID NO:4.

Yet other aspects of the invention relate to a nucleic acid encoding a heavy chain variable domain having at least 75% sequence identity (and up to 100% and any range therebetween) to a sequence selected from the group consisting of SEQ ID NO:2.

In yet another aspect, the present invention relates to a vector comprising the nucleic acid described herein.

In accordance with the present invention, the vector may be an expression vector.

Vector that contains the elements for transcriptional and translational control of the inserted coding sequence in a particular host are known in the art. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

In another aspect the present invention relates to an isolated cell which may comprise, the antibody or antigen binding fragment of the present invention, the nucleic acid or the vector described herein.

The isolated cell may comprise a nucleic acid encoding a light chain variable domain and a nucleic acid encoding a heavy chain variable domain either on separate vectors or on the same vector. The isolated cell may also comprise a nucleic acid encoding a light chain and a nucleic acid encoding a heavy chain either on separate vectors or on the same vector.

In accordance with the present invention, the cell may be capable of expressing, assembling and/or secreting an antibody or antigen binding fragment thereof.

In another aspect, the present invention provides a cell which may comprise and/or may express the antibody described herein.

In accordance with the invention, the cell may comprise a nucleic acid encoding a light chain variable domain and a nucleic acid encoding a heavy chain variable domain.

The cell may be capable of expressing, assembling and/or secreting an antibody or antigen binding fragment thereof.

The following examples are presented to illustrate the invention but it is not to be considered as limited thereto.

EXAMPLES

Production of Purified Monoclonal Anti-PSMA Antibodies:

Hybridomas producing the antibodies were cultured in Iscove's modified DMEM supplemented with 5% low IgG fetal bovine serum and 1 ng/mL of recombinant mouse interleukin-6. Cells were incubated in a humidified atmosphere at 37° C. with 5% $CO2$. After 30 days, mAb-containing hybridoma supernatant was clarified by centrifugation, brought to a final concentration of 20 mM Tris-HCI (pH 7.5) and passed through a 0.45 mm filter before being loaded onto a HiTrap protein G HP column, according to the manufacturer's instructions (GE Healthcare Biosciences, Piscataway, N.J.). After washing, bound MAb was eluted by using a low pH glycine buffer until the antibody is released. Fractions were collected and examined for protein content by monitoring the absorbance at 280 nm. Protein-containing fractions were pooled and subsequently dialyzed overnight against PBS at 4° C. The dialyzed protein solution was then concentrated to at least 1 mg/mL, supplemented with 10% glycerol and stored frozen at −20° C. The purity of each MAb was verified by Coomassie staining following SDS-PAGE.

Cloning of the Variable Regions of the Anti-PSMA Antibodies:

The nucleic acid and the amino acid sequence of the antibody's antigen binding site were determined. Total RNA from ten millions hybridoma cells was extracted and the first strand cDNA was synthesized by reverse transcription of the RNA using oligo(dT) primers. Then, the complete variable region of the antibody's light or heavy chain was obtained by 5'-rapid amplification of cDNA-ends with polymerase chain reaction using a gene specific oligonucleotide designed from the murine IgG constant 1 region. The resulting PCR product was cloned into the pGEM-T vector (Promega). Selected recombinant clones of the light or the heavy chains were sequenced and an Ig reading frame identified. The complementarity determining regions (CDR-L1, L2, L3 and H1, H2, H3) in the antibody sequence were identified by analyzing the amino acid sequence and following a set of rules based on the Kabat sequence definition, described in http://www.bioinf.org.uk.

Immunoreactivity of Murine Anti-PSMA Antibodies

A murine monoclonal anti-PSMA antibody comprising the heavy chain variable region depicted in SEQ ID NO.:2 and the light chain variable region depicted in SEQ ID NO.:4 was analyzed further (identified herein as mAb1).

Immunoreactivity of mAb1_against cancer cell line was tested by ELISA. Serially diluted purified antibody was tested on a cell membrane preparation that express PSMA (LNCaP) or not (PC-3). Results presented in FIG. 4 shows that the murine antibody reacts strongly with the LNCaP preparation but not with the PC-3 preparation.

Stability of Murine Anti-PSMA Antibodies

Proteins, including monoclonal antibodies, are a class of biological macromolecules that are often recognized as unstable when not in their native environment. Purified proteins often need to be stored for an extended period of time and upon long-term storage, biological material may not function properly or remain soluble and jeopardise their primary use as biological reagent or as drug or replacement therapy in human beings.

Figure 5:
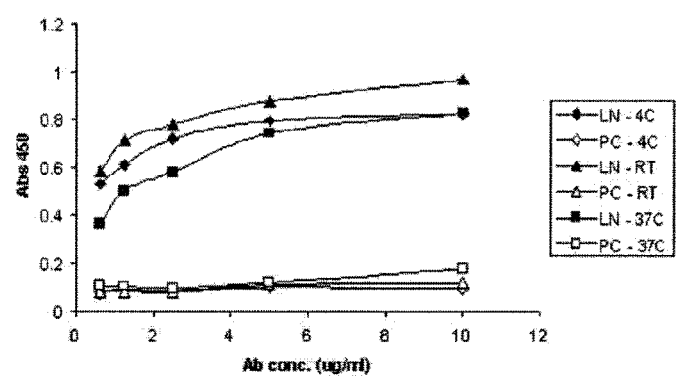
FIG. 5: Immunoreactivity of mAb1 to cancer cell line following storage at various temperatures. Purified antibody was stored at 4° C., room temperature or 37° C. for 3 months in sterile PBS pH7.4 and subsequently tested by ELISA on a cell membrane preparation that express PSMA (LNCaP) or not (PC-3). The antibody reacts in a nearly identical fashion in all 3 conditions.

The extent of storage or "shelf life" can vary widely, and is dependent on the nature of the protein and the storage condition used. The biological integrity of the purified mAb1 was evaluated by measuring its immunoreactivity by ELISA, subsequent to storage at different temperature. A stock of purified mAb1 at a concentration of 2.3 mg/ml in sterile PBS pH 7.4 was incubated for 3 months at a reference temperature of 4° C., at room temperature or at 37° C., in order to mimic extreme storage conditions or an extensive storage length. The graph in FIG. 5 shows that the curves of the antibody immunoreactivity are nearly superimposable in all the 3 conditions, indicating that the reactivity of mAb1 was maintained despite extreme storage condition at 37° C. for 3 months.

In Vitro and In Vivo Detection of PSMA-Tumor Cells with Murine Anti-PSMA Antibodies The murine anti-PSMA antibodies were used for detecting malignant prostatic tissue by immunohistochemistry.

Immunohistochemistry was performed on antigen retrieved, formalin fixed, paraffin embedded material. Formalin fixed paraffin embedded 5 µM sections were subjected to antigen retrieval in basic antigen retrieval solution (BD Pharmingen pH 9.5) in a microwavable pressure cooker for 10 min, cooled and equilibrated to 0.01M phosphate buffered saline (PBS) pH 7.4. Staining was carried out at room temperature in a humidified chamber. Endogenous peroxidases were inactivated with a 1% solution of $H_2O_2$ for 20 min, blocked with 5% normal goat serum (NGS) for 30 min and incubated with primary monoclonal antibodies (mAbs) diluted in PBS; 2% NGS overnight. Antibody binding to tissue sections was detected by the sequential addition of the following reagents followed by washing in PBS: goat anti-mouse IgG (H+L) (ICN) secondary antibody diluted 1:100 in PBS; 2% NGS for 1 hr, a complex of a bi-specific mAb mouse anti-peroxidase and horse radish peroxidase for 1 hr, and 3,3-diaminobenzidene tetrahydrochloride (DAB) at 0.6 mg/ml in PBS; 2% NGS; 0.01% $H_2O_2$ as chromogen. The primary antibodies were purified mAbs used at concentrations optimized in dilution experiments. mAb2 and mAb1 antibodies were used at 0.3 µg/ml, mAb6 at 0.16 ug/ml and mAb3 and mAb5 at 0.08 µg/ml. Mouse IgG mAb was used at a concentration of 0.2 µg/ml and served as a negative control for the primary antibodies.

Figure 6:
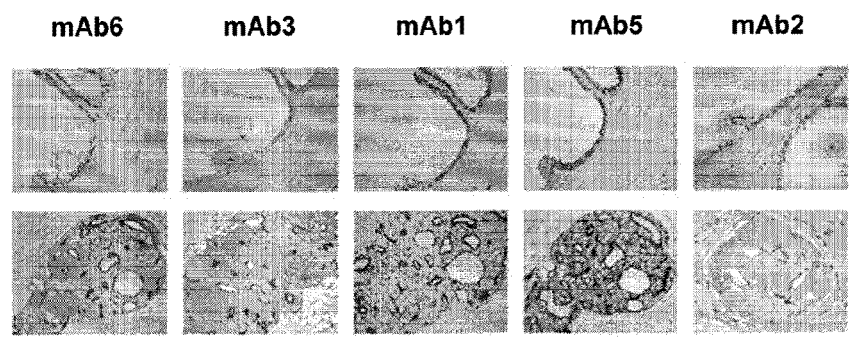
FIG. 6: Immunoreactivity of several murine monoclonal anti-PSMA antibodies against prostatic tissue. Immunoreactivity of the antibodies to the apical surface of prostatic acinar cells in benign (upper row), and malignant (lower row) prostatic tissues with more intense staining of cancer sections compared to benign.

Results presented in FIG. 6 shows that anti-PSMA antibodies are capable of staining malignant prostatic tissues.

For in vivo detection purposes the anti-PSMA antibodies were radiolabeled with Indium[111] through a chelating agent and administered to mouse bearing the LNCap graft (PSMA-expressing cells) and the PC-3 graft (non-PSMA expressing cells).

Antibody conjugation to DOTA: Purified monoclonal antibodies and all solutions were treated with the chelating resin Chelex (Bio-Rad) to remove trace metal ions from samples and buffers. Antibody was washed in 0.1M sodium phosphate buffer (pH 8.2) and concentrated to 3 mg/ml (30 000 MWCO Microcon; Millipore). Then, 50× molar excess of 1,4,7,10-Tetraazacyclododecane-1,4,7,10-tetraacetic acid mono(N-hydroxysuccinimide ester) (DOTA-NHS ester) in dimethylformamide (DMF) was added to the concentrated antibody preparation and the reaction mixture was incubated for 30 minutes at room temperature. The resultant antibody-DOTA conjugate was separated from the excess unreacted DOTA-NHS ester by repeated washing with 0.3M ammonium acetate buffer (pH 6.5) (30 000 MWCO Microcon; Millipore).

[111]In labelling of DOTA conjugate: Radiolabeling of the Ab-DOTA with $In^{111}$ was achieved by incubating 1 mCi of $^{111}InCl_3$ (MDS-Nordion) per 1 mg of Ab-DOTA for 1 h at 43° C. Then, the antibody was washed in PBS (pH 7.5) (Amicon Ultra 15) to remove the unchelated free $^{111}In$. The purity of the resulting Ab-DOTA-$In^{111}$ was determined by instant thin layer chromatography (ITLC-SG). A small portion (3 ul) of the radiolabeled product was spotted on a ITLC strip and the species were separated using a mobile phase consisting of a 1% solution of diethylene triamine pentaacetic acid (DTPA). Once the solvent front had reached an Rf value of approximately 0.9, the strip was removed from the mobile phase and cut in four equal portions, the bottom portion containing the Ab-DOTA with $In^{111}$ and the upper ones the free $In^{111}$. The strip portions were counted in a gamma counter in order to calculate the radio-purity and the specific activity of the conjugate. The radiopurity of the conjugate was calculated as 100×(cpm of bottom strip portion)/(total cpm of all strips), and reached >90%. The specific activity was calculated as the amount of radioactivity/quantity of protein, and reached 0.2-1 uCi/ug.

Figure 7:
FIG. 7: Tumor detection by SPECT of mouse bearing a LNCaP graft with labelled mAb1. CD-1 nude bearing subcutaneous LNCaP (left side of mouse image, 150 mm$^3$) or PC-3 (right side of mouse image, 18 mm$^3$) tumor xenograft were injected in the tail vein with 100 ug of a preparation of murine-DOTA radiolabeled with Indium-111. The specific activity of the radiolabeled conjugate was 1 uCi/ug and its radiopurity more than 95%. Images of the same mouse were obtained at the indicated post-injection time by a gamma camera.

In vivo biodistribution of Ab-DOTA-$In^{111}$ by scintigraphy: mice with visible tumor were administered, by tail vein injection, 20-100 ug of radiolabeled antibody, Ab-DOTA-$In^{111}$, or an equivalent amount of radioactivity of free $^{111}InCl_3$. At various times subsequent to the injection, mice were anaesthetized and the distribution of radioactivity was determined by scintigraphy of the whole mouse body. Image was acquired using a General Electric Millenium MG nuclear gamma camera from the ventral surface of the mouse body. Scintigraphy of the same animal were obtained at 24 and 48 h post-injection by gamma camera. FIG. 7 show the result of scintigraphy experiments using mAb1.

Treatment of Prostate Cancer Mouse Model with the Murine Anti-PSMA Antibody:

Mouse model bearing human prostate tumor was generated by inoculating 6-8 week old male balb/c mice subcutaneously at the right flank with the LNCaP tumor cells ($1 \times 10^7$) in 0.1 ml of PBS/Matrigel (Beckton-Dickinson, USA). The mice were kept in laminar flow rooms at a constant temperature of 22 C and 40-80% humidity. Animals had free access to sterile drinking water. Tumor size was measured in two dimensions using a calliper, and the volume was expressed in $mm^3$ using the formula: $V=0.536 a \times b^2$, where a and b are the long and short diameters of the tumor, respectively. The treatments were started at day 4 after tumor inoculation when the tumor size reached approximately 60-80 $mm^3$. Groups of 12 mice were each injected intravenously in the tail with 10 ul/g of either saline, a murine pool of IgG at 10 mg/ml or the anti- PSMA antibody at 10 mg/ml (mAb1). The treatment was administered twice a week for 3 consecutive weeks. The size of tumor was measured the day of the injection or at the same frequency after the treatment had cessed.

Figures 8A, 8B:
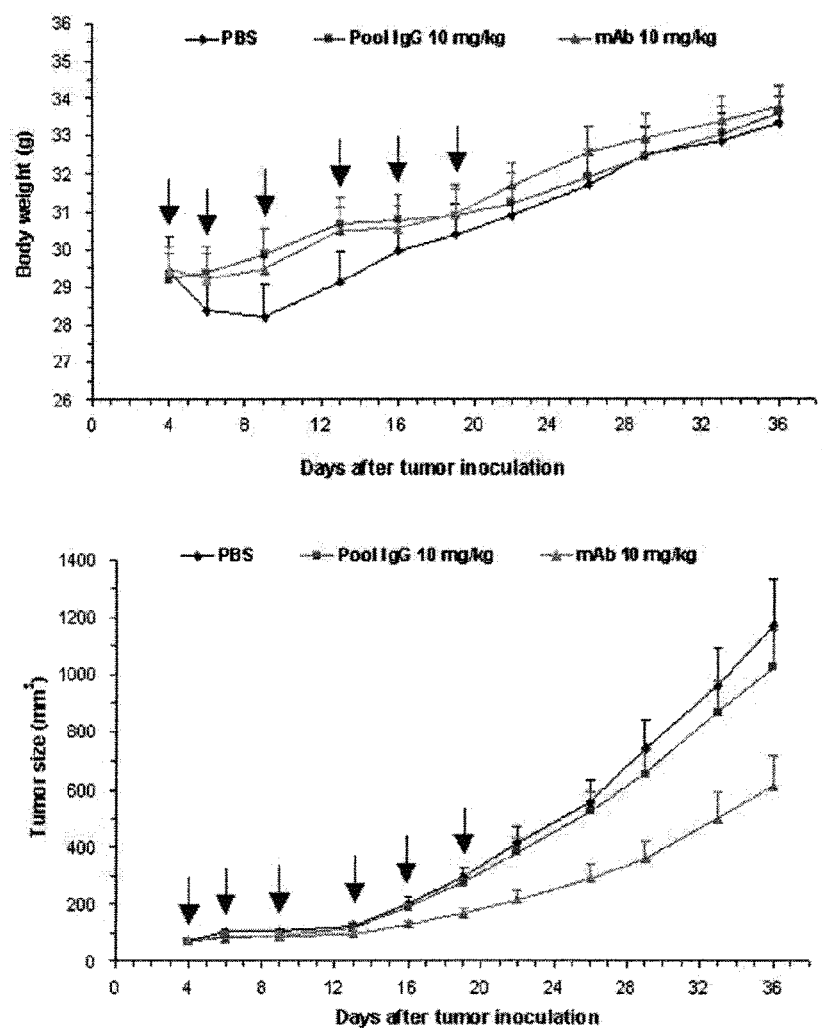
FIG. 8a: Body weight changes in the LNCaP tumor bearing mice in the different treatment groups including mice treated with mAb1. Arrows indicates a single injection.
FIG. 8b: In vivo antitumor effect of anti-PSMA antibody (mAb1) illustrated by a graph of the volume of LNCaP tumor over time. Arrows indicates a single injection.

FIG. 8a shows the graph of mouse body weight, and FIG. 8b tumor volume during and after the treatment period. The treatments did not cause any significant changes in the animal's body weight or suffered apparent side effects indicating the test articles were well tolerated by the tumor-bearing animals. No gross abnormalities were observed at the necropsy for these animals further indicating that the treatment is considered safe. The histopathologic examination of tissues from antibody-treated mice revealed no abnormal findings (not shown).

Mouse treated with saline or IgG had a similar tumor-growing rate until the last day of the experiment. The mean tumor size of the saline treated control mice reached 1171±162 mm$^3$ at 36 days after tumor inoculation, and the IgG treated group reached 1026±127 mm$^3$. In contrast, treatment with the anti-PSMA antibody produced a significant suppression of tumor growth rate that was prolonged long after the treatment had ceased. At the end of the experiment, the mean tumor volume of the anti-PSMA antibody-treated animals was 613±103 mm$^3$. As an indication of antitumor effectiveness, the tumor over control values (TIC) were calculated from the mean tumor size at the end of the experiment (Table I). The percentage T/C value reached 88% for the pool IgG and a statistically significant 52% for this anti-PSMA antibody.

TABLE I

Antitumor activity of anti-PSMA antibody (mAb1) in the treatment of LNCaP human prostate cancer xenograft.

| Treatment | Tumor size$^{a,b}$ at day 36 | T/C (%)$^c$ | P value |
|---|---|---|---|
| Vehicle | 1171 ± 162 | (—) | (—) |
| Pool IgG (10 mg/kg) | 1023 ± 127 | 88 | 0.443 |
| mAb (10 mg/kg) | 613 ± 103 | 52 | 0.005 |

$^a$Volume in mm$^3$
$^b$Mean ± SEM
$^c$Treated over control group

Overall, the results of this study indicate that the treatment of prostate cancer mouse model with this anti-PSMA antibody (mAb1).

Figure 9:
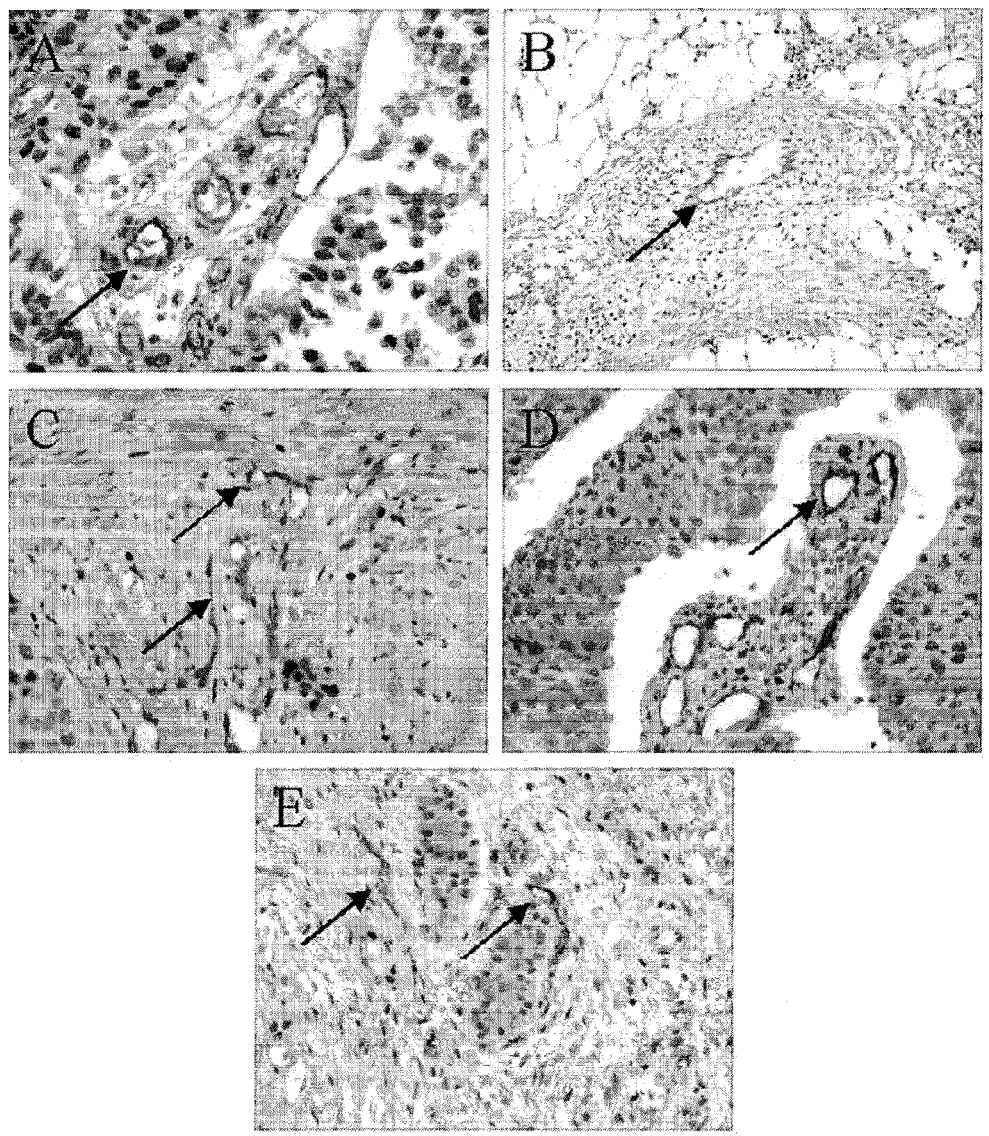
FIG. 9: Immunoreactivity of anti-PSMA antibody (mAb1) against tumor. a) bladder, b) colon, c) breast, d) lung, e) pancreas. Arrows indicates vascular-like structures.

Tissue Reactivity of the Murine Anti-PSMA Antibody:

Immunohistochemical evaluation was performed on different paraffin-embedded tumor tissue types, including transitional cell carcinomas of the urinary bladder, breast ductal carcinomas, colonic adenocarcinomas, large cell lung carcinomas, and pancreatic ductal adenocarcinomas (FIG. 9). After deparaffinization and rehydratation of slides, basic antigen retrieval was performed using Tris-HCl buffer pH 9.0. Prior to incubation with mAb1, the slides underwent 5 minutes incubation with 3% H$_2$O$_2$ and then UltraV block solution (Thermo Fisher Scientific Inc., CA). The slides were then incubated with the primary anti-PSMA antibody at 1 ug/ml in UltrAb diluent (Thermo Fisher Scientific Inc., CA) for 60 min at room temperature. The remainder of the immunohistochemical reaction was completed using UltraVision LP Value/HRP kit (Thermo Fisher Scientific Inc., CA). In all tissue sections, negative controls were performed using blocking reagents in place of the primary antibody.

In the bladder and lung tumors especially, very strong staining was clearly identified in the endothelial cells of small vessels, which may represent tumor neovasculature. Other tissues stained as follow: Breast tumor; some positive staining in small vascular-like spaces. Colon tumor; weak staining of endothelial cells in some large vessels and strong staining in slit-like structures, which may represent neovasculature. Bladder tumor; strong staining of vascular endothelial cells (and strong nuclear staining of most tumor cells. Lung tumor; strong staining of vascular endothelial cells in small vessels. Pancreatic tumor; positive staining in a few slit-like structures which may be vasculature.

Generation of Chimeric Anti-PSMA Antibodies

One problem in medical applications of murine antibody is that the human immune system recognizes the mouse antibody as foreign, and as a consequence, rapidly removes them from the circulation. Such response is recognized as producing human anti-mouse antibodies, or HAMA.

A solution to overcome this problem would be to generate antibodies with a higher content of human-derived sequence. Recombinant DNA technologies allows to take DNA that encodes the binding portion of murine monoclonal antibodies and fuse it with human antibody DNA, thus producing a gene that codes for a new antibody containing part murine and part human antibody sequence.

A chimeric antibody is constructed by the fusion of mouse variable domains to human IgG1 constant region such that the resulting antibody contains approximately 70% human sequences and 30% of murine origin. As a first stage, the antibody's cDNA for both the variable light and heavy region are cloned from a murine hybridoma cell pellet by a molecular biology technique known as 5'RACE, or rapid amplification of 5' complementary DNA ends. The resulting light and heavy chain cDNAs are then merged in frame with a human IgG1 light and heavy constant region. The resulting DNA construct is then ligated into an expression vector for cell transformation, ex, CHO cells, and protein production. FIG. 10 shows the deduced amino acid sequence of the light and heavy chains of a chimeric antibody comprising the variable regions of mAb1 (SEQ ID NO.:2 and SEQ ID NO.:4). This chimeric antibody is identified herein as chAb1.

Immunoreactivity and Specificity of Chimeric Anti-PSMA Antibodies

An ELISA assay was used to test the reactivity and specificity of purified chimeric anti-PSMA antibodies. Briefly, 96-well plates (Immulon 2HB) were coated overnight at 4° C. or for 2 h at 37° C. with 100 uL of PBS containing 5 ug of cell membrane preparation. Plates were washed four times with 200 uL of 10 mM Tris-HCl, 150 mM NaCl, and 0.1% Tween-20 (TBST, pH 7.5), and blocked for 1 h with 200 uL of TBST containing 5% FBS. Plates were then washed and incubated for 1 h at room temperature using 100 uL of serially diluted purified chimeric anti-PSMA antibodies in TBST containing 5% FBS. Antibody binding was detected by the sequential addition, followed by washing, of 100 uL of horseradish peroxidase (HRP) conjugated goat anti-human IgG whole molecule (Jackson Immunoresearch) diluted 1:5000 in TBST containing 5% FBS, for 1 h at room temperature, and 100 uL of HRP colorimetric substrate solution 3,3',5,5'-tetramethylbenzidine (BioFX Laboratories). The reaction was stopped with the addition of 100 uL of 0.5 M sulphuric acid and the absorbance was read at 450 nm in a microplate reader (BioTek Instruments).

A western blot was also carried out to determine the antibody specificity. The blot was blocked in 0.1% TBST containing 5% FBS, then probed with the chimeric antibody at a concentration of 1 ug/ml. Detection was performed using a HRP-conjugated anti-human IgG.

Figure 12:
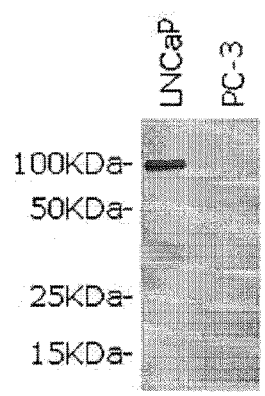
FIG. 12: Specificity of chAb1 for PSMA by Western blot analysis of LNCaP and PC-3 prostate cancer cells. The immunodetection reveal a single band at 100 KDa and corresponding to the molecular weight of PSMA in the LNCaP lysate only but not in the PC-3, suggesting that the antibody is specific for PSMA.

Results of the ELISA and western blot for chAb1 are presented in FIGS. 11A and 12 respectively. These results show that the chimeric antibodies has not lost its reactivity or specificity towards PSMA.

Results of the ELISA for a second chimeric antibody (chAb3) generated using the variable regions of mAb3 are presented in FIG. 11B.

Tissue Reactivity of the Chimeric Anti-PSMA Antibody:

The tissue reactivity of the chimeric anti-PSMA antibody chAb1 was compared with that of the murine anti-PSMA antibody mAb1.

Briefly, formalin-fixed paraffin embedded sections were subjected to basic antigen retrival in a microwave pressure cooker and equilibrated to 0.01M phosphate buffered saline pH 7.4 (PBS) and endogenous peroxidase were inactivated with a 1% solution of $H_2O_2$ in PBS. Tissue was blocked with 5% Normal Goat Serum (NGS) in 10 mM Tris-HCl, 150 mM NaCl, and 0.1% Tween-20 (TBST, pH 7.5) and incubated with primary antibodies diluted at 1 ug/ml in TBST containing 5% NGS. The antibody binding to tissue was detected by the sequential addition of the following reagents followed by washing in TBST; horseradish peroxidase (HRP) conjugated goat anti-mouse IgG whole molecule or HRP conjugated goat anti-human IgG whole molecule (Jackson Immunoresearch) diluted 1:500 in TBST containing 5% FBS, for 1 h at room and HRP colorimetric substrate solution ImmPACT DAB (Vector Lab).

Figure 13:
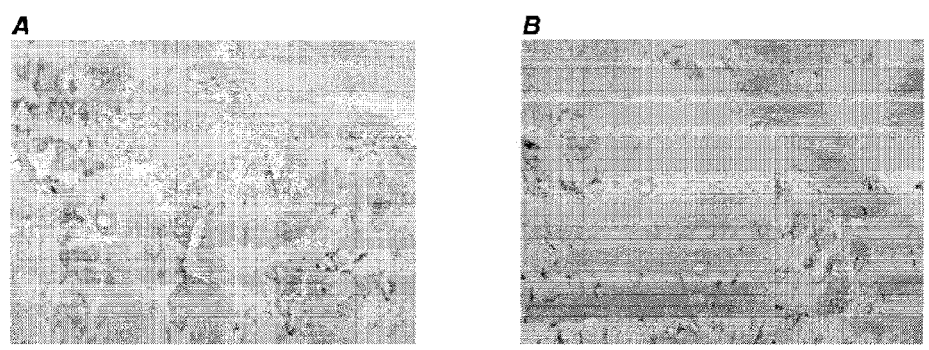
FIG. 13: The prostate cancer tissue reactivity of chAb1 is indistinguishable from the murine parental antibody (mAb1). The figures show the immunoreactivity of the murine (A: left) and the chimeric (B: right) antibody to the apical aspect of the secretory cells.

Results presented in FIG. 13 indicate that the prostate cancer tissue reactivity of the chimeric antibody (chAb1) is indistinguishable from the murine parental antibody (mAb1). The murine and chimeric antibody stain the apical side of secretory cells.

Immunoreactivity of DOTA-Conjugated Chimeric Antibody.

The chimeric anti-PSMA antibody (chAb1) was conjugated with DOTA (chAb1-DOTA) using a method similar to that described for the murine anti-PSMA antibody (see above).

Figure 14:
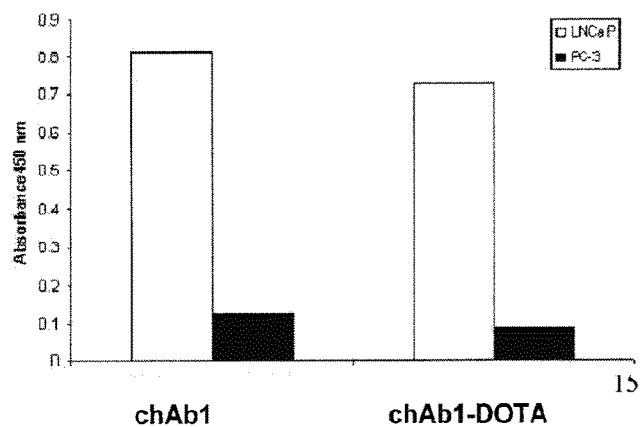
FIG. 14: Immunoreactivity of DOTA-conjugated chimeric antibody (chAb1). Purified antibody was conjugated to DOTA and the conjugate's reactivity was compared to the unconjugated antibody by ELISA on a cell membrane preparation that express PSMA (LNCaP) or not (PC-3). The fold reactivity of the DOTA conjugated antibody (chAb1-DOTA) on the LNCaP versus the PC-3 cell preparation is similar to that of the unconjugated antibody (chAb1) indicating that the DOTA conjugation did not interfere with the overall reactivity of the antibody.

The reactivity of the DOTA conjugated antibody (chAb1-DOTA) was compared to the unconjugated antibody (chAb1) by ELISA on a cell membrane preparation that express PSMA (LNCaP) or not (PC-3) (FIG. 14). The fold reactivity of the DOTA conjugated antibody on the LNCaP versus the PC-3 cell preparation is similar to that of the unconjugated antibody indicating that the DOTA conjugation did not interfere with the overall reactivity of the antibody.

Stability of the Chimeric Anti-PSMA Antibody

Figure 15:
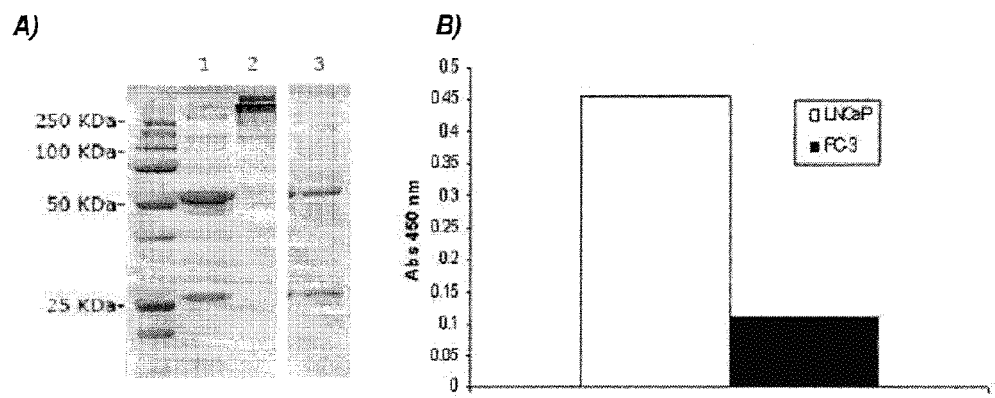
FIG. 15A: Stability of the chimeric antibody (chAb1). The purified chimeric antibody (chAb1) was incubated for a minimum of 5 days at −20° C. or 37° C. in two different buffer compositions. The preparation was then analysed by SDS-PAGE followed by Coomassie blue staining of the gel.
FIG. 15B: Immunoreactivity of the chimeric antibody (chAb1) in glycine buffer assessed by ELISA following a 5 days incubation at 37° C.

The purified chimeric antibody (chAb1) was incubated for a minimum of 5 days at −20° C. or 37° C. in two different buffer compositions. The preparation was then analysed by SDS-PAGE followed by Coomassie blue staining of the gel to visualise the molecular weight of the protein (left) (FIG. 15A). In lane 1 and 2, the antibody is in PBS pH7.4 and 10% glycerol. When stored at −20 C (lane 1), the gel reveal the two chains of the antibody at the expected molecular weight of 50 KDa and 25 KDa, while when incubated at 37° C., only high molecular weight species are visible (lane 2). The buffer composition of the antibody can overcome the formation of high molecular weight aggregates. Lane 3 reveals that when the antibody is incubated at 37° C. in a buffer consisting of 0.1M glycine buffered with Tris to pH 7.4, the individual 50 KDa and 25 KDa heavy and light chains can be distinguished, and aggregates are no more visible.

The immunoreactivity of the purified chimeric antibody (chAb1) in both buffers were assessed by ELISA following a 5 days incubation at 37° C. (FIG. 15B). When stored in glycine buffer, chAb1 shows a strong reactivity to PSMA-positive LNCaP cell membrane preparation and a minimal reactivity to PSMA-negative PC-3 (right), however, when stored in a PBS-glycerol buffer, non-specific reactivity to PC-3 cells increases dramatically which translate into a low signal to noise ratio (not shown).

The invention claimed is:

1. An antibody or antigen binding fragment comprising a heavy chain variable region comprising a CDRH1 as defined in SEQ ID NO.:5, a CDRH2 as defined in SEQ ID NO.:6, and a CDRH3 as defined in SEQ ID NO.:7, and a light chain variable region comprising a CDRL1 as defined in SEQ ID NO.:8, a CDRL2 as defined in SEQ ID NO.:9 and a CDRL3 as defined in SEQ ID NO.:10.

2. The antibody or antigen binding fragment of claim 1 comprising a light chain variable region as defined in SEQ ID NO.:4 and a heavy chain variable region as defined in SEQ ID NO.:2.

3. The antibody of claim 1, wherein the antibody is a naked antibody.

4. The antibody or antigen binding fragment of claim 1, wherein said antibody comprises a human constant region.

5. The antibody or antigen binding fragment of claim 4, wherein the human constant region is from a human IgG1.

6. The antibody or antigen binding fragment of claim 1 wherein said antibody or antigen binding fragment is stable at 37° C. for at least 3 months.

7. A pharmaceutical composition comprising the antibody or antigen binding fragment of 1 and a pharmaceutically acceptable carrier.

8. The pharmaceutical composition of claim 7, further comprising a therapeutic drug.

9. A method of treating a patient having a prostate tumor, the method comprising administering the antibody of claim 1.

10. The method of claim 9, wherein said antibody is conjugated with a theraputic moiety.

11. The antibody or antigen fragment of claim 1, wherein said antigen binding fragment is a FV, a Fab, a Fab' or a (Fab')$_2$.

12. The antibody or antigen fragment of claim 1, wherein said antibody or antigen binding fragment is conjugated with a therapeutic moiety.

13. The antibody or antigen fragment of claim 1, wherein said antibody or antigen binding fragment is conjugated with a detectable moiety.

14. A method of detecting prostate-specific membrane antigen-expressing cell, the method comprising administering the antibody or antigen binding fragment of claim 1 to a subject in need.

15. The method of claim 14, wherein said antibody or antigen binding fragment is conjugated with a detectable moiety.

* * * * *

UNITED STATES PATENT AND TRADEMARK OFFICE
CERTIFICATE OF CORRECTION

PATENT NO. : 8,629,247 B2
APPLICATION NO. : 13/264652
DATED : January 14, 2014
INVENTOR(S) : Moffett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Twenty-second Day of September, 2015

Michelle K. Lee
*Director of the United States Patent and Trademark Office*